US011883423B2

(12) United States Patent
Cui et al.

(10) Patent No.: US 11,883,423 B2
(45) Date of Patent: *Jan. 30, 2024

(54) NUCLEOBASE ANALOGUE DERIVATIVES AND THEIR APPLICATIONS

(71) Applicant: BOARD OF REGENTS, THE UNIVERSITY OF TEXAS SYSTEM, Austin, TX (US)

(72) Inventors: Zhengrong Cui, Austin, TX (US); Dharmika Lansakara-P., Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 11 days.

This patent is subject to a terminal disclaimer.

(21) Appl. No.: 17/539,682

(22) Filed: Mar. 14, 2022

(65) Prior Publication Data

US 2022/0193106 A1 Jun. 23, 2022

Related U.S. Application Data

(63) Continuation of application No. 16/576,127, filed on Sep. 19, 2019, now Pat. No. 11,219,633, which is a continuation of application No. 15/115,393, filed as application No. PCT/US2015/013454 on Jan. 29, 2015, now Pat. No. 10,463,684.

(60) Provisional application No. 61/933,035, filed on Jan. 29, 2014.

(51) Int. Cl.
*A61K 31/7068* (2006.01)
*C07D 401/04* (2006.01)
*A61K 47/54* (2017.01)
*C07H 19/073* (2006.01)

(52) U.S. Cl.
CPC ........ *A61K 31/7068* (2013.01); *A61K 47/542* (2017.08); *C07D 401/04* (2013.01); *C07H 19/073* (2013.01)

(58) Field of Classification Search
None
See application file for complete search history.

(56) References Cited

U.S. PATENT DOCUMENTS

| | | | |
|---|---|---|---|
| 5,216,142 A | 6/1993 | Horrobin et al. | |
| 5,795,909 A | 8/1998 | Shashoua et al. | |
| 6,960,648 B2 | 11/2005 | Bonny | |
| 10,463,684 B2 * | 11/2019 | Cui | A61K 31/7068 |
| 11,219,633 B2 * | 1/2022 | Cui | C07H 19/073 |
| 2002/0025943 A1 | 2/2002 | Bradley et al. | |
| 2002/0120100 A1 | 8/2002 | Bonny | |
| 2003/0032594 A1 | 2/2003 | Bonny | |
| 2007/0225248 A1 | 9/2007 | Myhren et al. | |
| 2008/0280851 A1 | 11/2008 | Myhren et al. | |
| 2009/0130214 A1 | 5/2009 | Couvreur et al. | |
| 2012/0088908 A1 | 4/2012 | Xue et al. | |
| 2013/0005678 A1 | 1/2013 | Sandvold et al. | |
| 2013/0053433 A1 | 2/2013 | Cho et al. | |
| 2013/0116209 A1 | 5/2013 | Isaacson et al. | |
| 2013/0131008 A1 | 5/2013 | Cui et al. | |
| 2015/0359811 A1 | 12/2015 | Paya Cuenca et al. | |

FOREIGN PATENT DOCUMENTS

| | | |
|---|---|---|
| WO | 1998032762 | 7/1998 |
| WO | 2006029081 A2 | 3/2006 |
| WO | 2009076761 A1 | 6/2009 |
| WO | 2010039039 A1 | 4/2010 |
| WO | 2011062503 A1 | 5/2011 |

OTHER PUBLICATIONS

International Search Report and the Written Opinion issued in International Application No. PCT/US2015/013454, dated Jun. 24, 2015.
International Preliminary Report on Patentability issued in International Application No. PCT/US2015/013454, dated Aug. 11, 2016.
"CID 24761020", PubChem, Compound Summary for CID 24761020, create date Apr. 7, 2008 [retrieved Mar. 12, 205].
Arshad, et al., "Potential applications of fish oils rich in n-3 fatty acids in the palliative treatment of advanced pancreatic cancer", Br J Nutr 106(6), 2011, 795-800.
Banker, G.S. et al., "Modern Pharmaceutics, 3ed", Marcel Dekker, New York, 1996, p. 596.
Barber, et al., "Fish oil-enriched nutritional supplement attenuates progression of the acute-phase response in weight-losing patients with advanced pancreatic cancer.", J Nutr 129(5), 1999, 1120-1125.
Barber, , "Metabolic response to feeding in weight-losing pancreatic cancer patients and its modulation by a fish-oil-enriched nutritional supplement", Clin Sci (Lond) 98(4), 2000, 389-399.
Barber, et al., "The effect of an oral nutritional supplement enriched with fish oil on weight-loss in patients with pancreatic cancer", Br J Cancer 81(1), 1999, 80-86.
Barber, et al., "Tolerance and incorporation of a high-dose eicosapentaenoic acid diester emulsion by patients with pancreatic cancer cachexia", Lipids 36(4), 2001, 347-351.
Beall HD et al. International Journal of Pharmaceutics. 1993, 93, 37-47.
Bergman, et al., "Antiproliferative activity, mechanism of action and oral antitumor activity of CP-4126, a fatty acid derivative of gemcitabine, in in vitro and in vivo tumor models", Invest New Drugs 29, 2011, 456-466.

(Continued)

*Primary Examiner* — Traviss C McIntosh, III
(74) *Attorney, Agent, or Firm* — Meunier Carlin & Curfman LLC

(57) ABSTRACT

Disclosed herein are derivatives of nucleobase analogues. The disclosed compounds have a nucleobase moiety and an omega-3 polyunsaturated fatty acid moiety, including pharmaceutically acceptable salt or prodrug thereof. Methods of using these compounds for the treatment of cancers such as pancreatic cancer are also disclosed.

20 Claims, 12 Drawing Sheets

(56) References Cited

OTHER PUBLICATIONS

Bergman, et al., "Determinants of resistance to 2',2'-difluorodeoxycytidine (gemcitabine)", Drug Resist Updat. 5(1), 2002, 19-33 (Abstract).
Bouffard, et al., "Kinetic studies on 2',2'-difluorodeoxycytidine (Gemcitabine) with purified human deoxycytidine kinase and cytidine deaminase", Biochem Pharmacol45(9), 1993, 1857-1861.
Bradley, , "Tumor Targeting by Covalent Conjugation of a Natural Fatty Acid to Paclitaxel", Clinical Cancer Research vol. 7., 2001, 3229-3238.
Bruera, et al., "Effect of fish oil on appetite and other symptoms in patients with advanced cancer and anorexia/cachexia: a double-blind, placebo-controlled study", J Clin Oncol 21(1), 2003, 129-134.
Bruns CJ et al. Neoplasia. 1999, 1(1), 50-62.
Brusa, et al., "Antitumor Activity and Pharmacokinetics of Liposomes Containing Lipophilic Gemcitabine Prodrugs", Anticancer Research 27, 2007, 195-200.
Burns, et al., "Phase I clinical study of fish oil fatty acid capsules for patients with cancer cachexia: cancer and leukemia group B study 9473", Cancer Res 5(12), 1999, 3942-3947.
Burris, et al., "Improvements in survival and clinical benefit with gemcitabine as first-line therapy for patients with advanced pancreas cancer: a randomized trial", J Clin Oncol 15(6), 1997, 2403-2413.
Dekoj, et al., "G2/M cell-cycle arrest and apoptosis by n-3 fatty acids in a pancreatic cancer model", J Surg Res 139(1), 2007, 106-112.
Dyrberg et al., In: Omega-3 Fatty Acids: Prevention and Treatment of Vascular Disease. 1995, Verona-Springer-Verlag, Kristensen et al., eds., Bi & Gi Publ., pp. 217-226.
Du, et al., "Cost analysis of pancreatic carcinoma treatment", Cancer 89(9), 2000, 1917-1924.
Falconer, et al., "Effect of eicosapentaenoic acid and other fatty acids on the growth in vitro of human pancreatic cancer cell lines", Br J Cancer69(5), 1994, 826-832.
Fearson, et al., "Effect of a protein and energy dense N-3 fatty acid enriched oral supplement on loss of weight and lean tissue in cancer cachexia: a randomised double blind trial", Gut 52(10), 2003, 1479-1486.
Frese, et al., "nab-Paclitaxel potentiates gemcitabine activity by reducing cytidine deaminase levels in a mouse model of pancreatic cancer", Cancer Discov 2(3), 2012, 260-269.
Funahashi, et al., "Opposing effects of n-6 and n-3 polyunsaturated fatty acids on pancreatic cancer growth", Pancreas 36(4), 2008, 353-362.
Garcia-Manteiga, et al., "Nucleoside transporter profiles in human pancreatic cancer cells: role of hCNT1 in 2',2'-difluorodeoxycytidine-induced cytotoxicity", Clin Cancer Res 9(13), 2003, 5000-5008.
Gregor, , "Does enteral nutrition of dietary polyunsaturated fatty acids promote oxidative stress and tumour growth in ductal pancreatic cancer? Experimental trial in Syrian Hamster", Prostaglandins Leukot Essent Fatty Acids 74(1), 2006, 67-74.
Harris, "Extending the cardiovascular benefits of omega-3 fatty acids." Curr Atheroscler Rep 7:375-80, 2005.
Heinemann, , "Inhibition of ribonucleotide reduction in CCRF-CEM cells by 2',2'-difluorodeoxycytidine", Mol Pharmacol38(4), 1990, 567-572.
Hering, et al., "Inhibition of proliferation by omega-3 fatty acids in chemoresistant pancreatic cancer cells.", Ann Surg Oncol 14(12, 2007, 3620-3628.
Holub, "Clinical nutrition: 4 omega-3 fatty acids in cardiovascular care," CMAJ 166(5):608-15, 2002.
Hsu CH et al. Pharm Res. 2003, 20(6), 918-925.
Huang, , "Action of 2',2'-difluorodeoxycytidine on DNA synthesis", Cancer Res 51 (22), 1991, 6110-6117.
Immordino, et al., "Preparation, characterization, cytotoxicity and pharmacokinetics of liposomes containing lipophilic gemcitabine prodrugs", Journal of Controlled Release 100(3), 2004, 331-346.

Jolly, , "Diet manipulation and prevention of aging, cancer and autoimmune disease.", Curr Opin Clin Nutr Metab Care 8(4), 2005, 382-387.
Jolly, et al., "Omega-3 polyunsaturated fatty acids and immunosenescence", Models of immunosenscence: Basic understanding and clinical applications, 2008, 1423-1426.
Kato T et al. Nutr Cancer 2007, 58(2), 178-187.
Kaye, et al., "Gemcitabine: current status of phase I and II trials", J Clin Oncol 12(8), 1994, 1527-1531.
Lansakara-P, et al., "Synthesis and in vitro evaluation of novel lipophilic monophosphorylated gemcitabine derivatives and their nanoparticles", International Journal of Pharmaceutics 429, 2012, 123-134.
Lanz C. et al. Journal of Seperation Science. 2007, 30: 1811-1820.
Lashinger L et al. Cancer Prevention Research. 2013, 6(10), 1046-1055.
Mackey, et al., "Functional nucleoside transporters are required for gemcitabine influx and manifestation of toxicity in cancer cell lines", Cancer Res 58(19), 1998, 4349-4357.
Merendino, et al., "Induction of apoptosis in human pancreatic cancer cells by docosahexaenoic acid", Ann N Y Acad Sci 1010, 2003, 361-364.
Merendino N et al. Biomed Res Int. 2013, 2013, 310186.
Miksad, et al., "Does a statistically significant survival benefit of erlotinib plus gemcitabine for advanced pancreatic cancer translate into clinical significance and value?", J Clin Oncol 25(28): 4506-4507; author reply 4508, 2007, 4506-4507.
Moore, et al., "Erlotinib plus gemcitabine compared with gemcitabine alone in patients with advanced pancreatic cancer: a phase III trial of the National Cancer Institute of Canada Clinical Trials Group", J Clin Oncol25(15):, 2007, 1960-1966.
Moses, et al., "Reduced total energy expenditure and physical activity in cachectic patients with pancreatic cancer can be modulated by an energy and protein dense oral supplement enriched with n-3 fatty acids", Br J Cancer 90(5), 2004, 996-1002.
Muniz, et al., "The ARF tumor suppressor inhibits tumor cell colonization independent of p53 in a novel mouse model of pancreatic ductal adenocarcinoma metastasis", Mol Cancer Res 9(7), 2011, 867-877.
Naguib YW et al. Mol Pharm. 2014, 11(4), 1239-1249.
Neff, et al., "Forced expression of cytidine deaminase confers resistance to cytosine arabinoside and gemcitabine.", Exp Hematol 24(11), 1996, 1340-1346.
O'Connor, et al., "Effect of dietary omega-3 and omega-6 fatty acids on development of azaserine-induced preneoplastic lesions in rat pancreas", J Natl Cancer Inst 81(11), 1989, 858-863.
Ohtaka, et al., "Ribonucleotide reductase subunit M1 is a possible chemoresistance marker to gemcitabine in biliary tract carcinoma", Oncol Rep 20, 2008, 279-286.
O'Keefe and Harris, Am J Cardiology 2000, 85:1239-41.
Olson, et al., "Epidemiology of pancreatic cancer and the role of family history", J Surg Oncol. 107(1), 2012, 1-7.
O'Neill, et al., "Costs and trends in pancreatic cancer treatment", Cancer 118(20), 2012, 5132-5139.
Owen SC. In: Rowe RC, Sheskey PJ, Owen SC Eds, Handbook of Pharmaceutical Excipients. London, Pharmaceutical Press, 2006; 32-35.
Pereira, , "Mechanism for ribonucleotide reductase inactivation by the anticancer drug gemcitabine.", J Comput Chem 25(10), 2004, 1286-1294.
Peters, et al., "Basis for effective combination cancer chemotherapy with antimetabolites", Pharmacol Ther 87(2-3), 2000, 227-253.
Radack et al., "The effects of low doses of omega-3 fatty acid supplementation on blood pressure in hypertensive subjects: a randomized controlled trial." Arch Intern Med 151:1173-80, 1991.
Rahman MM et al. Breast Cancer Res Treat. 2013, 141(3), 341-352.
Raut CP et al. Cancer Biol Ther. 2004, 3(12), 1217-1224.
Saif, , "U.S. Food and Drug Administration approves paclitaxel protein-bound particles (Abraxane(R)) in combination with gemcitabine as first-line treatment of patients with metastatic pancreatic cancer", Journal of the Pancreas 14(6), 2013, 686-688.

(56) References Cited

OTHER PUBLICATIONS

Shaikh, et al., "n-3 Polyunsaturated fatty acids exert immunomodulatory effects on lymphocytes by targeting plasma membrane molecular organization", Mol Aspects Med 33(1), 2012, 46-54.

Sloat, et al., "In vitro and in vivo anti-tumor activities of a gemcitabine derivative carried by nanoparticles", International Journal of Pharmaceutics 409, 2011, 278-288.

Spencer L et al. Eur J Cancer 2009, 45(12), 2077-2086.

Stillwell, et al., "Docosahexaenoic acid: membrane properties of a unique fatty acid", Chem Phys Lipids 126(1), 2003, 1-27.

Strouch, et al., "A high omega-3 fatty acid diet mitigates murine pancreatic precancer development", J Surg Res 165(1), 2011, 75-81.

Sugano and Michihiro, "Balanced intake of polyunsaturated fatty acids for health benefits." J Oleo Sci 50(5):305-11, 2001.

Van Moorsel, , "Combination chemotherapy studies with gemcitabine", Semin Oncol24 (2 Suppl 7): S7-17-S17-23, 1997.

Van Moorsel, et al., "Gemcitabine: Future Prospects of Single-Agent and Combination Studies", Oncologist 2(3), 1997, 1997.

Veltkamp, et al., "Oral administration of gemcitabine in patients with refractory tumors: a clinical and pharmacologic study", Clin Cancer Res14(11):, 2008, 3477-3486.

Von Hoff, et al., "Increased survival in pancreatic cancer with nab-paclitaxel plus gemcitabine.", 2013, 1691-1703.

Vonhoff, et al., "Gemcitabine plus nab-paclitaxel is an active regimen in patients with advanced pancreatic cancer: a phase I/II trial", J Clin Oncol 29(34), 2011, 4548-4554.

Wigmore, et al., "Effect of oral eicosapentaenoic acid on weight loss in patients with pancreatic cancer", Nutr Cancer 36(2), 2000, 177-184.

Wigmore et al. "The effect of polyunsaturated fatty acids on the progress of cachexia in patients with pancreatic cancer", Nutrition 12(1 Suppl): S27-30, 1996, 27-30.

Wolff, Manfred E. , "Burger's Medicinal Chemistry", 5ed, Part I, John Wiley & Sons, 1995, pp. 975-977.

Zhu, et al., "Lysosomal Delivery of a Lipophilic Gemcitabine Prodrug Using Novel Acid-Sensitive Micelles Improved Its Antitumor Activity", Bioconjugate Chem. dx.doi.org/10.1021/bc2005945.

Zhu S et al. Biomaterials. 2013, 34(9), 2327-2339.

* cited by examiner

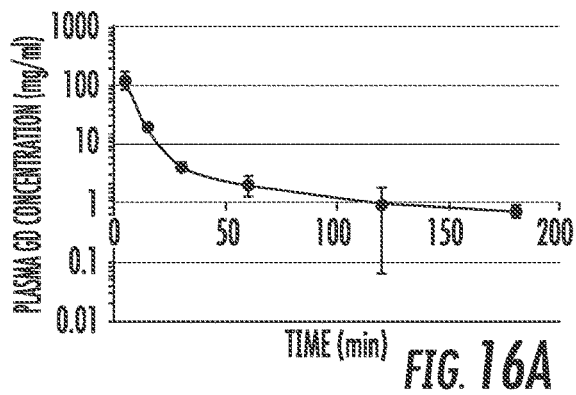
FIG. 16A
| PARAMETER | VALUE |
|---|---|
| A (μg/ml) | 334.5 |
| B (μg/ml) | 4.56 |
| α (min.$^{-1}$) | 0.205 |
| β (min.$^{-1}$) | 0.012 |
| $t_{1/2}\alpha$ | 3.38 |
| $t_{1/2}\beta$ | 57.75 |
| AUC (μg.min/ml) | 1998.3 |
| $K_{10}$(min.$^{-1}$) | 0.17 |
| $K_{12}$(min.$^{-1}$) | 0.033 |
| $K_{21}$(min.$^{-1}$) | 0.015 |
| $V_c$ (L/kg) | 0.221 |
| $C_{mix}$ | 339.05 |
| Cl(ml/min. kg) | 37.62 |
| $V_{ss}$ (L/kg) | 0.7 |
| MRT(min.) | 18.7 |
FIG. 16B
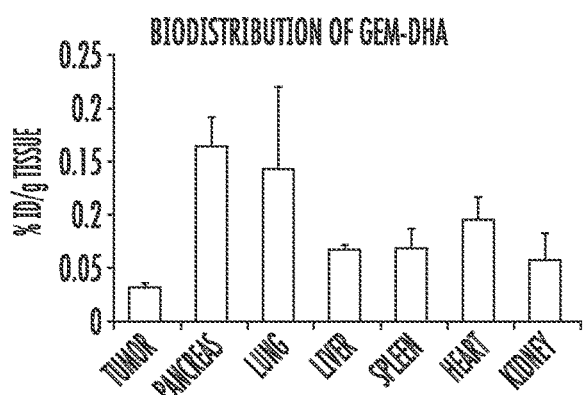
FIG. 16C
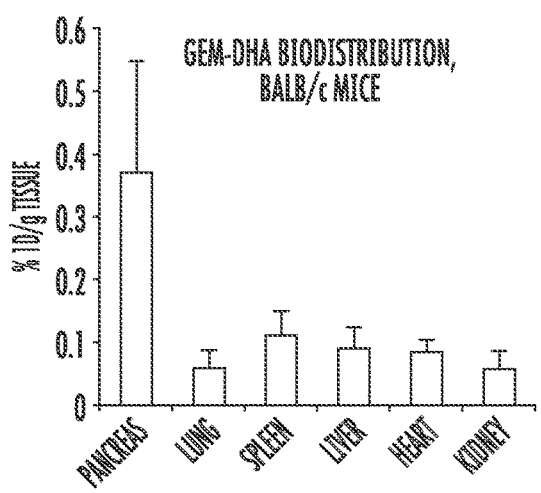
FIG. 16D
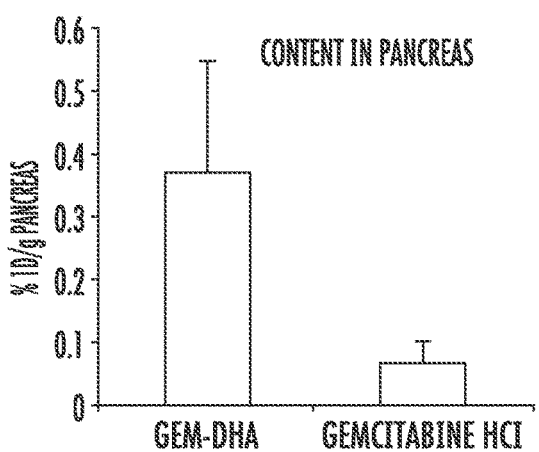
FIG. 16E

NUCLEOBASE ANALOGUE DERIVATIVES AND THEIR APPLICATIONS

CROSS-REFERENCE TO RELATED APPLICATIONS

This application is a continuation of U.S. patent application Ser. No. 16/576,127 filed Sep. 19, 2019 (now U.S. Pat. No. 11,219,633), which is a continuation of U.S. patent application Ser. No. 15/115,393 filed Jul. 29, 2016 (now U.S. Pat. No. 10,463,684), which is a U.S. national stage application filed under 35 U.S.C. § 371 of PCT/US2015/013454 filed Jan. 29, 2015, which claims the benefit of priority to U.S. Provisional Application No. 61/933,035 filed Jan. 29, 2014, all of which are hereby incorporated herein by reference in their entireties.

STATEMENT OF GOVERNMENT SUPPORT

This invention was made with government support under Grant No. CA135274 awarded by the National Institutes of Health. The government has certain rights in this invention.

BACKGROUND

Pancreatic cancer is the fourth most common cause of cancer-related deaths in the United States and the eight worldwide. The Pancreatic Cancer Action Network™ predicted that it will move from the $4^{th}$ to the $2^{nd}$ leading cause of cancer death in the US by 2020 or earlier, based on the changing demographics of the US population and changes in incidence and death rates. Pancreatic cancer has an extremely poor prognosis: for all stages combined, the 1- and 5-year relative survival rates are 25% and 6% respectively; for local disease the 5-year survival rate is approximately 15%, while the median survival for locally advanced and for metastatic disease, which collectively represent over 80% of individuals, is about 10 and 6 months respectively.

Globally, as of 2010, pancreatic cancer resulted in 310,000 deaths, up from 200,000 in 1990. In 2010, an estimated 43,000 people in the US were diagnosed with pancreatic cancer and almost 37,000 died from the disease. Pancreatic cancer has one of the highest fatality rates of all cancers, and is the fourth-highest cancer killer among both men and women worldwide.

Although it accounts for only 2.5% of new cases, pancreatic cancer is responsible for 6% of cancer deaths each year.

Early pancreatic cancer often does not cause symptoms, and the later symptoms are usually nonspecific and varied. Therefore, pancreatic cancer is often not diagnosed until it is advanced.

Treatment of pancreatic cancer depends on the stage of the cancer. Although localized cancer is considered suitable for surgery with curative intent at present, only 20% of cases present with localized disease at diagnosis. Surgery can also be performed for palliation, if the malignancy is invading or compressing the duodenum or colon. In such cases, bypass surgery might overcome the obstruction and improve quality of life but is not intended as a cure.

In patients not suitable for resection with curative intent, palliative chemotherapy may be used to improve quality of life and gain a modest survival benefit. Gemcitabine was approved by the United States Food and Drug Administration in 1998, after a clinical trial reported improvements in quality of life and a 5-week improvement in median survival duration in patients with advanced pancreatic cancer. This marked the first FDA approval of a chemotherapy drug primarily for a non-survivable clinical endpoint. Yet even with this positive progress, new therapies are still needed. New nucleobase compounds with improved properties can be useful in the treatment of pancreatic cancer as well as many other indications. The compounds and methods disclosed herein address these and other needs.

SUMMARY

In accordance with the purposes of the disclosed compounds, compositions and methods, as embodied and broadly described herein, the disclosed subject matter relates to compounds, compositions and methods of making and using the compositions. In more specific aspects, the disclosed subject matter relates to compounds that are derivatives of nucleobase analogues, methods of using the compounds, and compositions comprising the compounds. In certain aspects, the disclosed subject matter relates to compounds having the chemical structure shown in Formulas I-IV, as defined herein. In still further aspects, the disclosed subject matter relates to methods for treating cancer in a subject. For example, disclosed herein are methods whereby an effective amount of a compound or composition disclosed herein is administered to a subject having cancer, for example pancreatic cancer, and who is in need of treatment thereof.

Additional advantages will be set forth in part in the description that follows and the Figures, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DESCRIPTION OF FIGURES

(FIG. 2A) Concentration-time curves of Gem-DHA at room temperature (~22° C.) in a solution that contained 0%, 0.01%, or 0.04% (v/v) of Vitamin E As a control, the stability at 4° C. is also shown. (FIG. 2B) The effect of temperature on the chemical stability of Gem-DHA in a Tween 80/thanol/water formulation. (FIG. 2C) An Arrhenius plot showing the effect of temperature on the rate constant of the degradation of Gem-DHA in a Tween 80/ethanol/water formulation. In (FIG. 2B) and (FIG. 2C), the solution contained 0.9% (w/v) of sodium chloride. Data shown are the mean of at least 3 repeats, standard devisations not shown for clairty.

(FIG. 10A) IVIS images of tumors in the $1^{st}$ week and $4^{th}$ week after the initiation of treatment with Gem-DHA or gemcitabine HCl. (FIG. 10B) Tumor weights at the end of the study. (FIG. 10C) Photos of tumors at the end of the study. (FIG. 10D) Mouse body weight at various days after the implantation of tumor cells. Data shown in FIG. 10B and FIG. 10D are mean standard derivation (n=5-7). Four weeks after tumor implantation ($1\times10^6$ per mouse), mice with tumors were randomized into 3 groups (n=5-7) and intraperitoneally injected (i.p) with Gem-DHA (50 mg/kg, ~0.087 mole/kg), gemcitabine HCl (26.1 mg/ml, ~0.087 mole/kg), or left untreated. Gem-DHA was in a Tween 80/ethanol/water solution that contained 5% (w/v) of mannitol, and gemcitabine HCl was in a sterile mannitol solution (5%, w/v). Treatment was repeated twice a week for a total 7 doses. Thirty days after the first treatment, mice were euthanized and tumors were dissected.

FIG. 16A displays Gem-DHA plasma concentrations at various time points after it was i.v. injected into mice.

FIG. 16B displays selected pharmacokinetics parameters when data in FIG. 16A were fitted in two-compartment model.

FIG. 16C displays biodistribution profile of Gem-DHA in TC-1 tumor-bearing mice 90 min after i.v. injection (Gem-DHA dose is 75 mg/kg).

FIG. 16D displays biodistribution profile of Gem-DHA in healthy BALB/c mice 1 h after i.v. injection (Gem-DHA, 75 mg/kg).

FIG. 16E displays a comparison of the content of Gem-DHA and gemcitabine in the pancreas of healthy BALB/c mice 1 h after they were i.v. injected with Gem-DHA or gemcitabine HCl (75 mg/kg for both).

DETAILED DESCRIPTION

Figure 1:
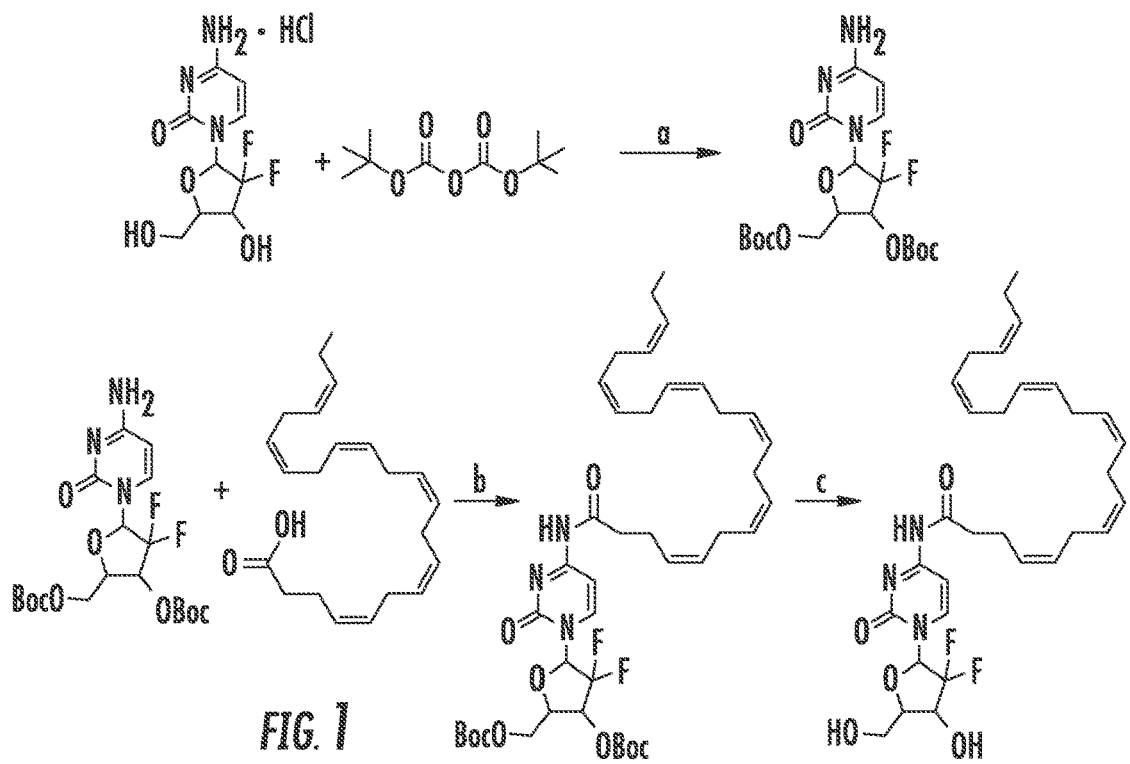
FIG. 1 depicts the synthesis of 4-(N)-DHA-Gem. The reagents and conditions are (a) KOH, 1,4-dioxane, 22° C.; (b) EDCl, HOAt, DCM, room temperature; and (c) TFA, DCM, room temperature.

The compounds, compositions and methods described herein may be understood more readily by reference to the following detailed description of specific aspects of the disclosed subject matter and the Examples and Figures included therein.

Before the present compounds, compositions and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., tumor growth or survival). The term "control" is used synonymously with the term "treat."

The term "anticancer" refers to the ability to treat or control cellular proliferation and/or tumor growth at any concentration.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups. The term "alkyl" as used herein is a branched or unbranched saturated hydrocarbon group of 1 to 24 carbon atoms, for example 1 to 3, 1 to 4, 1 to 5, 1 to 6, 1 to 7, 1 to 8, 1 to 9, 1 to 10, or 1 to 15 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ where $Z^1$ is alkyl as defined above.

The term "alkenyl" as used herein is a hydrocarbon group of from 2 to 24 carbon atoms, for example, 2 to 5, 2 to 10, 2 to 15, or 2 to 20 carbon atoms, with a structural formula containing at least one carbon-carbon double bond. Asymmetric structures such as $(Z^1Z^2)C=C(Z^3Z^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms, for example 2 to 5, 2 to 10, 2 to 15, or 2 to 20 carbon atoms, with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "carbonyl as used herein is represented by the formula —$C(O)Z^1$ where $Z^1$ can be a hydrogen, hydroxyl, alkoxy, alkyl, halogenated alkyl, alkenyl, alkynyl, aryl, heteroaryl, cycloalkyl, cycloalkenyl, heterocycloalkyl, or heterocycloalkenyl group described above. Throughout this specification "C(O)" or "CO" is a short hand notation for C=O.

The term "aldehyde" as used herein is represented by the formula —C(O)H.

The terms "amine" or "amino" as used herein are represented by the formula —$NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —$C(O)NZ^1Z^2$.

The term "carboxylic acid" as used herein is represented by the formula —C(O)OH. A "carboxylate" or "carboxyl" group as used herein is represented by the formula —$C(O)O^-$.

The term "ester" as used herein is represented by the formula —$OC(O)Z^1$ or —$C(O)OZ^1$, where $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1OZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1C(O)Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula —$NO_2$.

The term "silyl" as used herein is represented by the formula —$SiZ^1Z^2Z^3$, where $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2$Z$^1$, where Z$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "thiol" as used herein is represented by the formula —SH.

The term "thio" as used herein is represented by the formula —S—.

"R$^1$," "R$^2$," "R$^3$," "R$^n$," etc., where n is some integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compounds

Disclosed herein are compounds comprising a nucleobase analogue moiety and an omega-3 polyunsaturated fatty acid moiety, wherein the nucleobase analogue moiety is bonded to the omega-3 polyunsaturated fatty acid moiety, or a pharmaceutically acceptable salt or prodrug thereof.

A nucleobase analogue moiety can be any chemical that can substitute for a normal nucleobase in nucleic acids. Nucleobases are nitrogen-containing biological compounds (e.g., nitrogenous bases) found within deoxyribonucleic acid (DNA), ribonucleic acid (RNA), nucleotides, and nucleosides. The primary nucleobases are cytosine, guanine, adenine, thymine, and uracil. Adenine and guanine belong to the double-ringed class of molecules called purines. Cytosine, thymine, and uracil are all pyrimidines. Modified nucleobases include hypoxanthine, xanthine, 7-methylguanine, 5,6-dihyfrouracil, 5-methylcytosine, and 5-hydroxymethylcytosine.

Nucleobase analogues can comprise antimetabolites. An antimetabolite is a chemical that inhibits the use of a metabolite, which is another chemical that is part of normal metabolism. Such substances are often similar in structure to the metabolite they interfere with. The presence of antimetabolites can have toxic effects on cells, such as halting cell growth and cell division, so these compounds can be used as chemotherapy for cancer or to treat viral infections.

The compound formed when a nucleobase forms a glycosidic bond with the 1' anomeric carbon of ribose or deoxyribose is called a nucleoside, and a nucleoside with one or more phosphate groups attached at the 5' carbon is called a nucleotide. Thus, as used herein, nucleobase analogues include purine analogues, pyrimidine analogues, nucleoside analogues and nucleotide analogues.

Purine analogues are antimetabolites that mimic the structure of metabolic purines. Examples of purine analogues include, but are not limited to, azathioprine, mercaptopurine, thioguanine, flubarabine, pentostatin, and cladribine. Pyrimidine analogues are antimetabolites which mimic the structure of metabolic purines. Examples include, but are not limited to, 5-fluorouracil, floxuridine, cytosine arabinoside, and 6-azauracil.

Nucleoside analogues are molecules that act like the nucleosides in RNA or DNA synthesis. Once they are phosphorylated, they work as antimetabolites by being similar enough to nucleotides to be incorporated into growing RNA or DNA strands; but they can act as chain terminators. Example nucleoside analogues include, but are not limited to, (deoxy)adenosine analogues, (deoxy)cytidine analogues, (deoxy)guanosine analogues, (deoxy)thymidine analogues, (deoxy)uridine analogues, or combinations thereof. As used herein, for example, the term "(deoxy)adenosine" includes adenosine, deoxyadenosine, and combinations thereof. Other examples of nucleoside analogues include, but are not limited to, gemcitabine, fluororuacil, didanosine, vidarabine, cytarabine, emtricitabine, lamivudine, zalcitabine, abacavir, entecavir, stavudine, telbivudine, zidovudine, idoxuridine, trifluridine, apricitabine, or combinations thereof.

Polyunsaturated fatty acids (PUFAs) are fatty acids, i.e. a carboxylic acid with a long aliphatic tail, that contain more than one double bond in their backbone. Fatty acids have two ends, the carboxylic acid end, which is considered the beginning of the chain, thus "alpha", and the methyl end, which is considered the tail of the chain, thus "omega". The nomenclature of the fatty acid is taken from the location of the first double bond, counted from the methyl end, that is, the omega end. Therefore, omega-3 polyunsaturated fatty acids are those polyunsaturated fatty acids with a double bond at the third carbon atom from the end of the carbon chain. Examples of omega-3 PUFAs include, but are not limited to, alpha-linolenic acid (ALA), stearidonic acid (SDA), eicosatetroenoic acid (ETA), eicosapentaenoic acid (EPA), docosapentaenoic acid (DPA), and docosahexaenoic acid (DHA). In some embodiments, the omega-3 polyunsaturated fatty acids are chosen from docosahexaenoic acid, docosapentaenoic acid, eicosapentaenoic acid, alpha-linolenic acid, or combinations thereof. In other examples, the omega-3 polyunsaturated fatty acid is chosen from hexadecatrienoic acid, stearidonic acid, eicosatrienoic acid, eicosatetraenoic acid, heneicosapentaenoic acid, tetracosapentaenoic acid, and tetracosahexaenoic acid or combinations thereof.

Polyunsaturated fatty acids (PUFAs), including omega-3, omega-6 and omega-9 fatty acids, are vital to everyday life and function. For example, the beneficial effects of omega-3 fatty acids like all-cis-5,8,11,14,17-eicosapentaenoic acid (EPA) and all-cis-4,7,10,13,16,19-docosahexaenoic acid (DHA) on lowering serum triglycerides are well established. All-cis-9,12,15-octadecatrienoic acid (ALA) is the precursor essential fatty acid of EPA and DHA. All-cis-5,8,11,14-eicosatetraenoic acid (AA) and its precursors all-cis-6,9,12-octadecatrienoic acid (GLA) and all-cis-9,12-octadecadienoic acid (LA) have been shown to be beneficial to infants.

Various of these compounds are also known for other cardioprotective benefits such as preventing cardiac arrhythmias, stabilizing atherosclerotic plaques, reducing platelet aggregation, and reducing blood pressure. See e.g., Dyrberg et al., In: Omega-3 Fatty Acids: Prevention and Treatment of Vascular Disease. Kristensen et al., eds., Bi & Gi Publ., Verona-Springer-Verlag, London, pp. 217-26, 1995; O'Keefe and Harris, *Am J Cardiology* 2000, 85:1239-41; Radack et al., "The effects of low doses of omega-3 fatty acid supplementation on blood pressure in hypertensive subjects: a randomized controlled trial." *Arch Intern Med* 151:1173-80, 1991; Harris, "Extending the cardiovascular benefits of omega-3 fatty acids." *Curr Atherospcler Rep* 7:375-80, 2005; Holub, "Clinical nutrition: 4 omega-3 fatty acids in cardiovascular care," *CMAJ* 166(5):608-15, 2002. Indeed, the American Heart Association has also reported that omega-3 fatty acids can reduce cardiovascular and heart disease risk. Other benefits of PUFAs are those related to the prevention and/or treatment of inflammation and neurodegenerative diseases, and to improved cognitive development. See e.g., Sugano and Michihiro, "Balanced intake of polyunsaturated fatty acids for health benefits." *J Oleo Sci* 50(5):305-11, 2001.

In light of the health benefits of PUFAs it is desirable to find new ways to deliver these and other beneficial materials to a subject. However, the hydrophobicity and oxidative stability (e.g., PUFAs are sensitive to oxidation) characteristics associated with many PUFAs creates significant challenges for incorporating them into compositions.

It is understood that reference herein to a particular PUFA bonded to the nucleobase analogue moiety can be a mixture of PUFA's. For example, certain fish oils, squid oils, seal oils, krill oils, rapeseed oil, flax, fungal oils, and algal oils can contain mixtures of omega-3, 6, and/or 9 fatty acids. These mixtures can be used and conjugated to nucleobase analogues, as disclosed herein.

In some embodiments, the omega-3 polyunsaturated acid moiety can be bonded directly to the nucleobase analogue moiety. For example, a compound as disclosed herein can be represented by the formula: $CH_3—CH_2—CH=CH—Z—C(O)—XZ^1$ wherein Z is a $C_3$-$C_{40}$ alkyl or alkenyl group comprising at least one double bond and $Z^1$ is nucleobase analogue moiety, and X is NH or O. In some embodiments, there is an additional ligand or spacer between the nucleobase analogue moiety and the omega-3 polyunsaturated acid moiety. Thus, $Z^1$ can be 1 to 10 atom linker and then nucleobase moiety.

In some examples, the nucleobase analogue comprises gemcitabine. Chemically, gemcitabine is a nucleoside analogue, specifically a deoxycytidine analogue, in which the hydrogen atoms on the 2' carbon of deoxycytidine (a deoxyribonucleoside, a component of DNA) are replaced by fluorine atoms, as shown below.

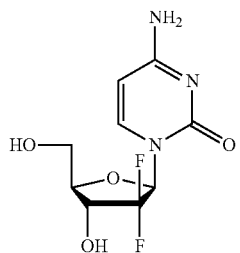

As with fluorouracil and other analogues of pyrimidines, the triphosphate analogue of gemcitabine replaces one of the building blocks of nucleic acids, in this case cytidine, during DNA replication. The process arrests tumor growth, as only one additional nucleoside can be attached to the "faulty" nucleoside, resulting in apoptosis. Another target of gemcitabine is the enzyme ribonucleotide reductase (RNR). The diphosphate analogue binds to RNR active site and inactivates the enzyme irreversibly. Once RNR is inhibited, the cell cannot produce the deoxyribonucleotides required for DNA replication and repair, and cell apoptosis is induced.

Disclosed herein are compounds having Formula I:

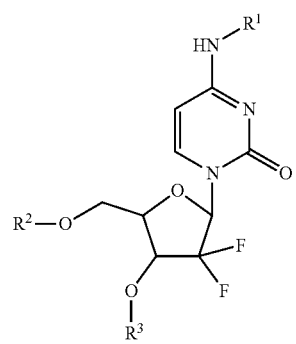

wherein $R^1$, $R^2$, and $R^3$ are independently selected from hydrogen, halogen, hydroxyl, amino, thiol, thioalkyl, alkyl, alkenyl, alkynyl, haloalkyl, cycloalkyl, heterocycloalkyl, alkylaryl, aryl, alkylheteroaryl, heteroaryl, or omega-3 polyunsaturated fatty acid, any of which is optionally substituted with acetyl, alkyl, amino, amido, alkoxyl, alkylhydroxy, cycloalkyl, heterocycloalkyl, aryl, heteroaryl, carbonyl, halogen, hydroxyl, thiol, cyano, or nitro;

with proviso that at least one of $R^1$, $R^2$, or $R^3$ comprises an omega-3 polyunsaturated fatty acid; or a pharmaceutically acceptable salt or prodrug thereof.

In some examples, the one or more omega-3 polyunsaturated fatty acid is bound directly to the gemcitabine-type compound. In some embodiments, there is an additional ligand or spacer between the one or more omega-3 polyunsaturated fatty acid and the gemcitabine-type compound.

In some examples, $R^1$, $R^2$ and $R^3$ each independently comprise an omega-3 polyunsaturated fatty acid. In some examples, at least one of $R^1$, $R^2$, or $R^3$ is $CH_3—CH_2—CH=CH—Z—C(O)—X—$ wherein Z is a $C_3$-$C_{40}$ alkyl or alkenyl group comprising at least one double bond and X is NH or O. In other examples, at least one of $R^1$, $R^2$, or $R^3$ is $CH_3—CH_2—CH=CH—Z—C(O)—X—L—$ wherein Z is a $C_3$-$C_{40}$ alkyl or alkenyl group comprising at least one double bond, and L is a 1-10 atom linker, such as an alkyl or alkoxyl linker, and X is NH or O. In some examples, $R^1$ and $R^2$ each independently comprise an omega-3 polyunsaturated fatty acid while $R^3$ does not comprise an omega-3 poly unsaturated fatty acid. In some examples $R^2$ and $R^3$ each independently comprise an omega-3 polyunsaturated fatty acid, while $R^1$ does not comprise an omega-3 poly unsaturated fatty acid. In some examples $R^1$ and $R^3$ each independently comprise an omega-3 polyunsaturated fatty acid, while $R^2$ does not comprise an omega-3 poly unsaturated fatty acid. In some examples $R^2$ comprises an omega-3 polyunsaturated fatty acid while $R^1$ and $R^3$ do not comprise an omega-3 poly unsaturated fatty acid. In some examples $R^3$ comprises an omega-3 polyunsaturated fatty acid, while $R^1$ and $R^2$ do no comprise an omega-3 poly unsaturated fatty acid. In some examples, $R^1$ comprises an omega-3 poly unsaturated fatty acid, while $R^2$ and $R^3$ do not comprise an omega-3 poly unsaturated fatty acid.

In some examples of Formula I, where $R^2$ and $R^3$ are hydrogen, the compounds have Formula II:

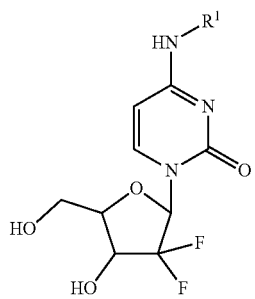

II wherein $R^1$ comprises an omega-3-polyunsaturated acid which is optionally substituted with acetyl, alkyl, amino, amido, alkoxyl, alkylhydroxy, cycloalkyl, heterocycloalkyl, aryl, heteroaryl, carbonyl, halogen, hydroxyl, thiol, cyano, or nitro;

or a pharmaceutically acceptable salt or prodrug thereof. For example, disclosed are compounds of Formula II where $R^1$ is $CH_3$—$CH_2$—CH=CH—Z—C(O)—X— wherein Z is a $C_3$-$C_{40}$ alkyl or alkenyl group comprising at least one double bond, and X is NH or O.

In some examples of Formula II, $R^1$ comprises docosahexaenoic acid, compounds are of Formula III:

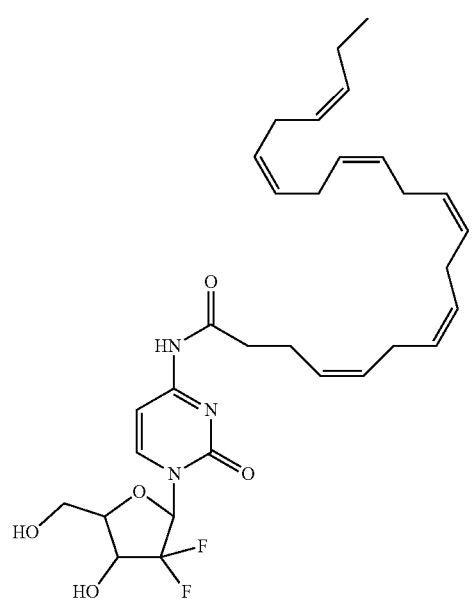

III or a pharmaceutically acceptable salt or prodrug thereof.

In some examples of Formula II, $R^1$ comprises eicosapentaenoic acid, compounds are of Formula IV:

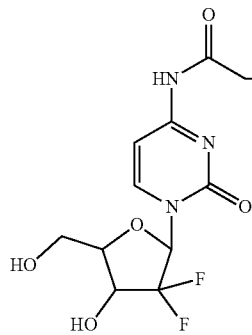

IV or a pharmaceutically acceptable salt or prodrug thereof.

Also disclosed herein are pharmaceutically-acceptable salts and prodrugs of the disclosed compounds. Pharmaceutically-acceptable salts include salts of the disclosed compounds that are prepared with acids or bases, depending on the particular substituents found on the compounds. Under conditions where the compounds disclosed herein are sufficiently basic or acidic to form stable nontoxic acid or base salts, administration of the compounds as salts can be appropriate. Examples of pharmaceutically-acceptable base addition salts include sodium, potassium, calcium, ammonium, or magnesium salt. Examples of physiologically-acceptable acid addition salts include hydrochloric, hydrobromic, nitric, phosphoric, carbonic, sulphuric, and organic acids like acetic, propionic, benzoic, succinic, fumaric, mandelic, oxalic, citric, tartaric, malonic, ascorbic, alpha-ketoglutaric, alpha-glycophosphoric, maleic, tosyl acid, methanesulfonic, and the like. Thus, disclosed herein are the hydrochloride, nitrate, phosphate, carbonate, bicarbonate, sulfate, acetate, propionate, benzoate, succinate, fumarate, mandelate, oxalate, citrate, tartarate, malonate, ascorbate, alpha-ketoglutarate, alpha-glycophosphate, maleate, tosylate, and mesylate salts. Pharmaceutically acceptable salts of a compound can be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of Formulas I-IV can be prepared beginning from gemcitabine HCl. For example, the hydroxyl groups of gemcitabine can be protected allowing for nucleophilic acyl substitution between the amine group of gemcitabine and the carboxylic acid group of the polyunsaturated fatty acid. Then the protecting groups can be removed to give the gemcitabine-polyunsaturated fatty acid compound.

Methods of Use

Gemcitabine (2', 2'-difluorodeoxycytidine, dFdC) is a deoxycytidine analogue. It is approved by the United States Food and Drug Administration for the treatment of various solid tumors including ovarian cancer, non-small cell lung cancer, pancreatic cancer, and breast cancer. It is also an attractive candidate for combination therapy due to its favorable toxicity profile. Combinations of gemcitabine with cisplatin, etoposide, ormitomycin are active against many other solid tumors such as bladder cancer, gastric cancer, and esophageal cancer. Gemcitabine for injection is marketed by Eli Lily as Gemzar™. Gemzar™ is still widely used, and various generic formulations are currently available. However, the generics do not improve the antitumor activity of gemcitabine.

Intravenous (i.v.) gemcitabine has been the standard care for advanced pancreatic cancer for years. Pancreatic cancer is the fourth leading cause of cancer-related death in the U.S., with 10% 1-year survival following diagnosis, and a median survival of 5.6-6 months. Expected new cases diagnosed in the U.S. jumped from 28,300 to 44,000 between 1999 and 2012, with mortality rates as high as incidence rates (10.9/100,000 and 12/100,000, respectively). Clinically, pancreatic carcinoma is classified into three categories: resectable, locally advanced (unresectable), and metastatic (distant), with median survivals of 15.2, 5.8, and 2.6 months, respectively. Surgical resection is the only curative option, but unfortunately 80-90% of tumors are not resectable at the time of diagnosis. For locally advanced disease, radio- or chemotherapy can be given to shrink the tumor to enhance resectability, while in metastatic disease, the use of palliative radio- and/or chemotherapy cannot extend the median survival beyond 3-6 months. Gemzar™ has been the standard care for advanced pancreatic cancer for many years, although the 12-month survival remains as low as 18%. There have been numerous clinical trials to test the feasibility of integrating other anticancer drugs into gemcitabine therapy, mostly with disappointing results. The oral HER1/EGFR tyrosine kinase inhibitor erlotinib, in combination with gemcitabine, only prolonged the median survival by 10 days (Miksad RA et al. *J Clin Oncol.* 2007, 25(28), 4506-4508; Moore MJ et al. *J Clin Oncol.* 2007, 25(15), 1960-1966; O'Neill CB et al. *Cancer.* 2012, 118(20), 5132-5139). The highest 12-month survival achieved in clinical trials (~48%) was with a combination of Abraxine® and gemcitabine (Von Hoff DD et al. *J Clin Oncol.* 2011, 29(34), 4548-4554).

Upon injection, over 90% of gemcitabine is deaminated, extracellularly and intracellularly, to 2', 2'-difluorodeoxyuridine (dFdU) by deoxycytidinedeaminases (dCDA). The dFdU is thought to be related to the adverse toxicity of gemcitabine. Gemcitabine is highly hydrophilic and transported into cells by nucleoside transporters such as the human equilibrative nucleoside transporter-1 (hENT1). After cellular uptake, gemcitabine is phosphorylated by a deoxycytidine kinase (dCK) into gemcitabine monophosphate (dFdCMP), which is further phosphorylated to gemcitabine diphosphate (dFdCDP) and then gemcitabine triphosphate (dFdCTP). The dFdCTP inhibits DNA synthesis, while dFdCDP acts as a ribonucleotide reductase (RNR) inhibitor, decreasing cellular dNTP pool and leading to increased incorporation of dFdCTP into DNA.

Omega-3 PUFAs such as docosahexaenoic acid (DHA), eicosapentaoeoic acid (EPA), and α-linolenic acid (ALA), are a group of fatty acids that are thought to be beneficial in the prevention and treatment of various human diseases, including heart disease, autoimmune disease, and cancer. DHA is considered the most potent omega-3 PUFA because it has the longest chain (22 carbons) and the highest degree of unsaturation (6 double bonds). Most of DHA's beneficial effects are attributed to its potent anti-inflammatory properties; however, there is increasing evidence that DHA can inhibit cancer cell growth directly. DHA has other benefits as well, including reducing cachexia in cancer patients (i.e., cancer-related loss of appetite, weight, and quality of life). Indeed, data from multiple clinical trials have shown that oral consumption of fish oil rich in the omega-3 PUFAs, such as DHA and EPA, alleviates tumor-related cachexia and improves the quality of life of pancreatic cancer patients.

Further provided herein are methods of treating or preventing cancer in a subject, comprising administering to the subject an effective amount of a compound or composition as disclosed herein. Further provided herein are methods of treating or preventing cancer in a subject, comprising administering to the subject an effective amount of a composition comprising any of the compounds disclosed herein.

Methods of killing a tumor cell are also provided herein. The methods comprise contacting a tumor cell with an effective amount of a compound or composition as disclosed herein. The methods can further include administering a second compound or composition (e.g., an anticancer agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation. Methods of treating inflammation in a subject are further provided herein, the methods comprising administering to the subject an effective amount of a compound or composition as described herein. Optionally, the methods can further include administering a second compound or composition (e.g., an anti-inflammatory agent).

The disclosed subject matter also concerns methods for treating a subject having an oncological disorder or condition. In one embodiment, an effective amount of one or more compounds or compositions disclosed herein is administered to a subject having an oncological disorder and who is in need of treatment thereof. The disclosed methods can optionally include identifying a subject who is or can be in need of treatment of an oncological disorder. The subject can be a human or other mammal, such as a primate (monkey, chimpanzee, ape, etc.), dog, cat, cow, pig, horse, mouse or other animals having an oncological disorder. Means for administering and formulating compounds for administration to a subject are known in the art, examples of which are described herein. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include B cell cancers such as leukemia (acute lymphoblastic, acute myeloid, chronic lymphocytic, chronic myeloid, and other), lymphoma (Hodgkin's and non-Hodgkin's), and multiple myeloma.

Other examples of cancers that can be treated according to the methods disclosed herein are adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma—hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lung cancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/ multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenstrom's macroglobulinemia, and Wilms' tumor.

The disclosed subject matter also concerns methods for treating a subject having a viral infection or disorder. Viral infections include, but are not limited to, infections due to hepatitis B virus, hepatitis C virus, herpes simplex virus, human immunodeficiency virus (HIV), varicella zoster, poxviruses, hepadnaviruses, rhabdoviruses, RNA tumor viruses, lentiviruses, oncoviruses, human papillomavirus, Epstein-Barr virus, Kaposi's sarcoma-associated herpesvirus, human T-lymphotropic virus, Merkel cell polyomavirus, smallpox, parvovirus, human bocavirus, BK virus, JC virus, human astrovirus, Norwalk virus, coxsackievirus, hepatitis A virus, poliovirus, rhinovirus, sever acute respiratory syndrome (SARS) virus, yellow fever virus, dengue virus, West Nile virus, Rubella virus, Hepatitis E virus, Influenza virus, guanatiro virus, junin virus, lassa virus, machupo virus sabia virus, Crimean-Congo hemorrhagic fever virus, ebola virus, Marburg virus, measles virus, mumps virus, parainfluenza virus, respiratory syncytial virus, human metapneumovirus, hendra virus, nipah virus, rabies virus, hepatitis D virus, rotavirus, orbivirus, coltivirus, and banna virus.

Other examples of diseases caused by viral infections that can be treated according to the methods disclosed herein can include acute febrile pharyngitis, paryngocunjunctival fever, epidemic keratoconjunctivitus, infantile gastroenteritis, aseptic meningitis, pericarditis, myocarditis, infectious mononucleosis, Bukitt's lymphoma, Hodgkin's lymphoma, nasopharyngeal carcinoma, acute hepatitis, chronic hepatitis, hepatic cirrhosis, hepatocellular carcinoma, primary HSV-1 infection, latent HSV-1 infection, herpes labialis, primary HSV-2 infection, latent HSV-2 infection, cytomegalic inclusion disease, Kaposi sarcoma, multicentric castleman disease, primary effusion lymphoma, AIDS, influenza, Reye syndrome, measles, postinfectious encephalomyelitis, mumps, hyperplastic epithelial lesions, cervical carcinoma, squamous cell carcinomas, croup, pneumonia, bronciolitis, common cold, poliomyelitis, rabies, bronchiolitis, german measles, congenital rubella, chickenpox, herpes zoster, shingles, and hand, foot and mouth disease.

Further provided herein are methods of treating or preventing cachexia in a subject, comprising administering to the subject an effective amount of a compound or composition as disclosed herein. Cachexia or wasting syndrome is loss of weight, muscle atrophy, fatigue, weakness and significant loss of appetite in someone who is not actively trying to lose weight. Cachexia is seen in subjects with conditions including, but not limited to, cancer, AIDS, chronic obstructive lunch disease, multiple sclerosis, congestive heart failure, tuberculosis, familial amyloid polynueropathy, mercury poisoning and hormonal deficiency. Cachexia is a positive risk factor for death, meaning if the subject has cachexia, the chance of death from the underlying conditions is increased dramatically. Currently, there are no widely accepted drugs to treat cachexia.

Compositions, Formulations and Methods of Administration

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 100% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use.

Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively, or an immunotherapeutic such as ipilimumab and bortezomib. In other aspect, the disclosed compounds are coadministered with other HDAC inhibitors like ACY-1215, Tubacin, Tubastatin A, ST-3-06, OR ST-2-92.

In certain examples, compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts or prodrugs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

The examples below are intended to further illustrate certain aspects of the systems and methods described herein, and are not intended to limit the scope of the claims.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process.

Proton NMR spectra were recorded on a 300 MHz Varian UNITY Plus or a 500 MHz Varian INOVA. Chemical shifts ($\delta$) of $^1$H NMR spectra were recorded in parts per million (ppm) relative to tetramethylsilane (TMS), which was the reference ($\delta$=0 ppm). $^1$H NMR data are reported according to the following order: chemical shift, integration (i.e., number of hydrogen atoms), multiplicity (s=singlet, d=doublet, t=triplet, q=quartet, m=multiplet, br=broad, brs=broad singlet), and coupling constant in Hertz (Hz). High resolution mass spectra were acquired in electron spray positive and negative ionization modes by direct injection onto an IonSpec 9.4T QFT-FTMS system.

All commercially available chemical reagents were purchased from Sigma-Aldrich (St. Louis, MO) or Thermo Fisher Scientific Inc. (Pittsburgh, PA) and were used as received unless noted. Gemcitabine HCl was from U.S. Pharmacopeia (Rockville, MD) or Biotang, Inc. (Lexington, MA). Cis-4,7,10,13,16,19-docosahexaenoic acid (DHA) and trifluoroacetic acid (TFA) were from Acros Organics (Morris Plains, NJ). Di-tert-butyl-dicarbonate, 1-(3-dimethylaminopropyl)-3-ethylcarbodiimide hydrochloride ($EDC_1$), 3-(4,5-dimethylthiazol-2-yl)-2,5-diphenyltetrazolium bromide (MTT), HPLC grade methanol, and Tween 80 were from Sigma-Aldrich (St Louis, MO). Hydroxy-7-azabenzotriazole (HOAt) was from CreoSalus, Inc. (Louisville, KY). Isopropyl myristate (IPM) was from TCI America (Montgomeryville, PA). Anhydrous sodium sulfate, ammonium chloride, mono- and di-basic sodium phosphates, ethyl acetate, HPLC-grade acetonitrile, dichloromethane (DCM), acetone, hexane, and octanol were from Thermo Fisher (Waltham, MA). BD Matrigel™ Basement Membrane Matrix was from BD Biosciences (San Jose, CA). D-Luciferin K$^+$ salt bioluminescent substrate was from Perkin Elmer (Waltham, MA). Guava Nexin reagent for flow cytometry was from EMD Millipore (Billerica, MA). Lactate dehydrogenase (LDH) cytotoxicity detection kit was from Takara Clontech Laboratories, Inc. (Mountain View, CA). Dulbecco's modified Eagle medium (DMEM), Roswell Park Memorial Institute (RPMI1640) medium, fetal bovine serum (FBS), horse serum, penicillin, streptomycin, Dulbecco's phosphate buffer saline (DPBS) were all from Invitrogen-Life Technologies (Carlsbad, CA). All other chemicals, reagents, and solvents were of analytical grade and used as received without further purification. Air or moisture-sensitive reactions were performed under an atmosphere of argon. Thin-layer chromatography (TLC) on Whatman silica gel plates (UV254) from Fisher Scientific was used to monitor the reaction progress. Silica gel—grade 60 (230-400 mesh) from Fisher Scientific was used for column chromatography to purify reaction products. The chemical structures of final compounds were confirmed using NMR and high resolution mass spectrometry.

TC-1 mouse lung, Panc-02 mouse pancreatic, BxPC-3 and MIA PaCa-2 human pancreatic cancer cell lines were from the American Type Culture Collection (ATCC, Manassas, VA). Panc-1-Luc human pancreatic cell line was generously provided by Dr. Dawn E. Quelle at the University of Iowa (Muniz VP et al. *Mol Cancer Res.* 2011, 9(7), 867-877). TC-1 and Panc-02 cells were grown in RPMI 1640 medium. BxPC-3, MIA PaCa-2, and Panc-1-Luc cells were grown in DMEM, and the DMEM for MIA PaCa-2 cells was supplemented additionally with 2.5% horse serum. All media were supplemented with 10% FBS, 100 U/ml of penicillin, and 100 g/ml of streptomycin.

HPLC analyses of Gem-DHA were performed using an Agilent Infinity 1260 (Agilent Corp., Santa Clara, CA) with a RP-C$_{18}$ column (Zorbax Eclipse, 5 µm, 3 mm×150 mm, Santa Clara, CA). The mobile phase was methanol and water (90:10, v/v). The flow rate was 1.0 ml/min, and the detection wavelength was 248 nm. When mouse plasma or tissue samples were used, the mobile phase was methanol and 1% (v/v) acetic acid in water (85:15, v/v) with a flow rate of 1.2 ml/min To analyze gemcitabine in biological samples, the method reported by Lanz et al. was followed with modifications (Lanz C. et al. *Journal of Seperation Science.* 2007, 30: 1811-1820). Briefly, an Agilent 1260 Infinity HPLC Station equipped with an Agilent quaternary pump and an Agilent Diode array UV detector was used. An Agilent C-18 reversed-phase column was used (Zorbax Eclipse Plus C18, 5 µm, 3×150 mm) at a controlled temperature of 20° C. The detection wave length was 248 nm. The mobile phases were solution A (phosphate buffer, pH adjusted to 3.0 using phosphoric acid) and solution B (acetonitrile). The column was equilibrated using solution A prior to each run for at least 30 min at a flow rate of 0.6 ml/min, followed by another 30 min at 1.2 ml/min. The gradient elution consisted of 100% solution A for 6 min, followed by a gradual change to 97% solution A and 3% solution B over 1 min. This composition was maintained for 2 min, and the composition was returned back to 100% solution A over 1 min, and left to run for 10 more minutes to let the column to equilibrate to the initial condition before starting a new sample. The flow rate was 1.2 ml/min.

Statistical analyses were completed using analysis of variance followed by Fischer's protected least significant difference procedure. A p-value of<0.05 (two-tail) was considered statistically significant.

Example 1

Synthesis and Characterization of 4-(N)-Docosahexaenoyl Difluorodeoxycytidine (4-(N)-DHA-Gem, DHA-Gem or Gem-DHA)

The 4-(N)-DHA-Gem was synthesized following a previously reported conjugation scheme with slight modifications (Sloat BR et al. *Int J of Pharmaceutics.* 2011, 409(1-2), 278-288; Lansakara-P DSP et al. *Int J Pharmaceutics.* 2012, 429(1-2), 123-134) (FIG. 1). Gemcitabine HCl (1) (200 mg, 0.67 mmol) in 13.3 mL of 1 N potassium hydroxide was cooled to 4° C. (Ohtaka, KN et al. *Oncol Rep.* 2008, 20, 279-286). To this solution, di-tert-butyl dicarbonate (Boc$_2$O, 1.483 g, 6.8 mmol) in about 13.3 mL of anhydrous dioxane was added over 10 min under argon atmosphere. The reaction mixture was stirred at room temperature (~22° C.) for 1 h and extracted with ethyl acetate (EtOAc). The organic layer was washed with brine, dried over anhydrous sodium sulfate (Na$_2$SO$_4$) and filtered. Solvent was removed under reduced pressure. The residue was added to Boc$_2$O (1.483 g, 6.8 mmol) in 13.3 mL of anhydrous dioxane and 13.3 mL of 1 M KOH at room temperature. The reaction was monitored by thin-layer chromatography (TLC). After 1 h, the reaction mixture was extracted to EtOAc. The organic layer was washed with brine, dried over anhydrous Na$_2$SO$_4$, and filtered. Solvent was removed, and the crude product was purified by column chromatography (dichloromethane (DCM) to acetone, 1:1, v/v). The desired product fractions were pooled and dried to yield 219 mg of 3',5'-O-bis(tert-butoxycarbonyl) gemcitabine. $^1$H NMR (500 MHz, acetone-d$^6$) δ 7.60 ($^1$H, d, J=7.6 Hz, 6-CH), 6.34 (1H, brs, 1'-CH), 5.97 (1H, d, J=7.6 Hz, 5-CH), 5.29 (1H, brs, 3'-CH), 4.53-4.39 (3H, m, 4'-CH, 5'A-CH, 5'B-CH), 2.82 (2H, s, NH2) 1.50, 1.47 (18H, two s, (CH$_3$)3C). A solution of 3',5'-O-bis(tert-butoxycarbonyl) gemcitabine (150 mg, 324 µmol), DHA (123 mg, 373.9 µmol) and HOAt (75 mg, 551.1 µmol) in anhydrous DCM was pre-cooled to 4° C., and 1-ethyl-3-(3-dimethylaminopropyl)carbodiimide (EDCI) (93.75 mg, 604.1 µmol) was added. The mixture was degassed by vacuum sonication and then stirred at room temperature under argon for about 40 h. Water (5 mL) was added to the reaction mixture and extracted three times with a mixture of EtOAc and hexane (2:1, v/v). The combined organic phase was washed with saturated ammonium chloride (NH$_4$Cl) and brine and then dried over anhydrous Na$_2$SO$_4$. The solvent was evaporated, and the residue was purified by column chromatography (EtOAc:Hexane, 3:7, v/v). The conjugated amide was isolated and quantified (~165 mg). $^1$H NMR was as follows: (300 MHz, acetone-d$^6$) δ 9.18 (1H, s, NHCO), 7.83 (1H, d, J=7.8 Hz, 6-CH), 7.49 (1H, d, J=7.8 Hz, 5-CH), 6.47-6.42 (1H, m, 1'-CH), 5.42-5.30 (12H, m, CH$_2$), 5.30-5.05 (1H, m, 3'-CH), 4.50-4.34 (3H, m, 4'-CH and 5'-CH), 2.90-2.79 (10H, m, CH$_2$), 2.60-2.40 (4H, m, CH$_2$), 2.07 (2H, p, J=7.5 Hz, CH$_2$), 1.53-1.46 (18H, m, (CH$_3$)$_3$C), 0.97 (3H, t, J=7.4 Hz, terminal CH$_3$). To a stirred solution of the conjugated amide (37 mg, 47.8 nmol) in 3 mL of DCM, about 0.2 mL of trifluroacetic acid (TFA) was added. This solution was stirred at room temperature for 4 h, and excess TFA was removed under reduced pressure. The concentrated sample was co-distilled with DCM for 3 times. The crude sample was chromatographed on silica gel (DCM:ethanol, 94:6, v/v) (Immordino, MLP et al. *J Contolled Release.* 2004, 100(3), 331-346; Lansakara-P, DSP et al. *Int J Pharmaceutics.* 2012, 429(1-2), 123-134). The desired fractions were pooled, and the solvent was evaporated to yield 4-(N)-Gem-DHA (Gem-DHA, ~80 mg, ~36% of original combined weights of gemcitabine and DHA). $^1$H NMR was as follows: (300 MHz, THF-d$^4$) δ 10.13 (1H, s, NHCO), 8.17 (1H, d, J=7.5 Hz, 6-CH), 7.37 (1H, d, J=7.5 Hz, 5-CH), 6.25 (1H, t, J=7.4 Hz, 1'-CH), 5.51-5.27 (12H, m, CH), 4.40-4.20 (1H, m, 3'-CH), 3.95-3.70 (3H, m, 4'-CH and 5'-CH), 2.95-2.82 (10H, m, CH$_2$), 2.50-2.41 (4H, m, CH$_2$), 2.08 (2H, p, J=7.2 Hz, CH$_2$), 0.96 (3H, t, J=7.7 Hz, terminal CH$_3$). ESI-HRMS [M+Na]+m/z calculated for $C_{31}H_{41}F_2N_3NaO_5$: 596.29065, found: 596.29068.

The purity of the synthesized compound was confirmed by LC/MS following gradient elution. The LC/MS system used was an Agilent Technologies 6530 Accurate Mass Quadruple TOF LC/MS using a RP $C_{18}$ column (Agilent Zorbax, 50×2.1 mm, 5 μm) at 40° C. The mobile phase consisted of solvent A (water with 0.1% formic acid) and solvent B (acetonitrile with 0.1% formic acid). Mobile phase composition was changed from 95% solvent A to 100% solvent B over 5 min, ran for 2 more minutes, and finally changed back to 95% solvent A over 4 more minutes. The flow rate was 0.7 ml/min. The target compound was detected at 4.85 min, and the compound was observed as [M+H]$^+$ m/z at 574.3, [M+Na]$^{+\ m/z\ at}$ 596.3, [2M+H]$^+$ m/z at 1147.6, and [2M+Na]$^+$ m/z at 1169.6. Minor traces (<0.2%) of the starting materials (i.e., DHA or gemcitabine) or the oxidized forms of Gem-DHA were found in the LC/MS spectra.

The aqueous solubility of Gem-DHA was determined following an indirect method according to Beall et al. with minimal modifications (Beall HD et al. *International Journal of Pharmaceutics*. 1993, 93, 37-47). Briefly, an excess amount of Gem-DHA was added to 100 μl of IPM in a crimp-sealed amber glass vials under nitrogen and was stirred vigorously at room temperature for 24 h, protected from light. After the stirring was stopped, the mixture was left to stand for an additional 24 h for equilibration. The content of the vial was centrifuged (14,000 rpm, 10 min) and the supernatant was transferred into a different tube. Aliquots of the saturated IPM solution were used to measure the Gem-DHA concentration before partitioning ($A_1$) using HPLC (after proper dilution with methanol). Then, water was added to the IPM saturated solution in a volume ratio of 10:1. The two phases were mixed by vortexing for 5 min, left to stand for 15 min, then centrifuged (14,000 rpm, 15 min) to collect the IPM layer. Gem-DHA concentration in the IPM layer ($A_2$) was again measured using HPLC after partitioning. The following equation was used to calculate the partition coefficient ($K_{IPM/water}$) (Beall HD et al. *International Journal of Pharmaceutics*. 1993, 93, 37-47):

$$K_{IPM/water} = \left[\frac{A_1}{(A_1 - A_2)}\right] \times \left(\frac{V_{water}}{V_{IPM}}\right) \quad (1)$$

where $V_{water}$ is the volume of the water phase and $V_{IPM}$ is the volume of IPM. The value of ($V_{water}/V_{IPM}$) was 10.

The aqueous solubility ($S_w$) of Gem-DHA was determined using the following equation (Id.):

$$S_w = \frac{S_{IPM}}{K_{IPM/water}} \quad (2)$$

where $S_{IPM}$ is the solubility of Gem-DHA in IPM. Gem-DHA was found to be stable in IPM under test conditions for at least 48 hours (>92% remaining)

In order to validate the method of Beall et al. (Id.), the aqueous solubility of 4-(N)-stearoyl gemcitabine, another lipophilic gemcitabine conjugate (Sloat BR et al. *Int J Pharm*. 2011, 409(1-2), 278-288), which is stable in water, was measured directly (i.e., direct method) or using the indirect method reported by Beall et al. (Beall HD et al. *International Journal of Pharmaceutics*. 1993, 93, 37-47). The solubility of 4-(N)-stearoyl gemcitabine in water was found to be 1.38±1.6 μg/ml when measured directly, 1.39±0.1 μg/ml when measured using the indirect method (Table 1). Therefore, the indirect method was used to estimate the solubility of Gem-DHA in water, which was found to be 25.15±11.2 μg/ml (Table 1).

TABLE 1

Water solubility of Gem-DHA and GemC18.

| Compound | $K_{IPM/water}$ | Water Solubility Indirect method | Direct method |
|---|---|---|---|
| Gem-DHA | 194.72 ± 111.3 | 25.15 ± 11.2 | N/A |
| Stearoyl gemcitabine (GemC18) | 35.33 ± 2.7 | 1.39 ± 0.1 | 1.38 ± 1.6 |

Data shown are mean ± standard deviation (n = 3).

The octanol-water partition coefficient of Gem-DHA was determined using a previously reported method with minor modifications (Hsu CH et al. *Pharm Res*. 2003, 20(6), 918-925). Briefly, octanol and PBS (7.4, 0.01 M) were mutually saturated for 24 h. Gem-DHA was dissolved in octanol (0.4 mg/ml, PBS-saturated) and 10 μl of the solution were withdrawn and diluted with methanol to measure Gem-DHA concentration using HPLC ($C_1$) PBS was added to octanol at a volume ratio ($V_{PBS}/V_{oct}$) of 20:1 into a sealed vial under nitrogen, and the mixture was agitated vigorously at room temperature using a horizontal orbital shaker at 250 rpm (Max Q 2000, Thermo Scientific, Waltham, Mass.) while protected from light. After 5 h, the mixture was centrifuged (14,000 rpm, 15 min) and the concentration of Gem-DHA in the octanol layer was determined using HPLC ($C_2$). Partition coefficient ($K_{oct/water}$) was calculated using the following equation:

$$K_{oct/water} = \left[\frac{C_1}{(C_1 - C_2)}\right] \times \left(\frac{V_{PBS}}{V_{oct}}\right) \quad (3)$$

Gem-DHA was found to be stable in octanol under the test conditions for at least 18 h.

The partition coefficient (octanol/PBS 7.4) of Gem-DHA was also measured using an indirect method by determining the concentration of the drug in octanol, before and after partitioning. The logP value (i.e., the octanol/water partition coefficient) of Gem-DHA was found to be 2.24±0.25.

Gem-DHA is freely soluble in ethanol or Tween 80. Gem-DHA was solubilized into an aqueous formulation that contains Tween 80 (10%, w/v) and ethanol (5.5%, v/v) (referred to as the Tween 80/ethanol/water formulation) to evaluate its in vivo activity. The stability of Gem-DHA in this formulation was evaluated in crimp-sealed amber glass vials under nitrogen atmosphere. Briefly, 150 μl of the Gem-DHA aqueous solution at a concentration of about 7 mg/ml were added to the amber glass vials under nitrogen atmosphere, and the vials were crimp-sealed with aluminum seals over rubber lids. At predetermined time intervals, 10 μl of the solution were diluted with 90 μl of methanol and mixed, and the concentration was measured using HPLC. Stability tests were carried out at room temperature (~22° C.) or 4° C. in triplicates. Vitamin E was added in the formulation to a final concentration of 0.01% or 0.04% (v/v) to evaluate the effect of vitamin E on the chemical stability of Gem-DHA.

Figure 2A:
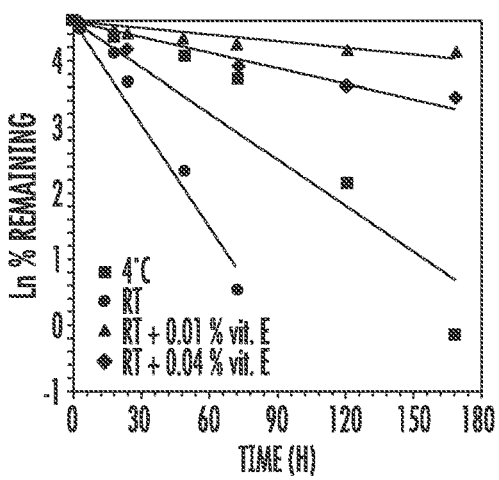
FIG. 2A-FIG. 2C depict the chemical stability of Gem-DHA in Tween 80/ethanol/water.

Gem-DHA solubilized in the Tween 80/ethanol/water formulation was found to degrade at room temperature (~22° C.) (FIG. 2A). The degradation was slower at 4° C. The degradation was also slower in the presence of vitamin E, and vitamin E at 0.01% (w/v) was more effective than at 0.04% (w/v). Indeed, it was reported that a higher concentration of vitamin E may not necessarily have a higher anti-oxidative activity, as higher concentrations may sometimes lead to opposite effects (Owen S C. In: Rowe R C, Sheskey P J, Owen S C Eds, Handbook of Pharmaceutical Excipients. London, Pharmaceutical Press, 2006; 32-35).

Figure 2B:
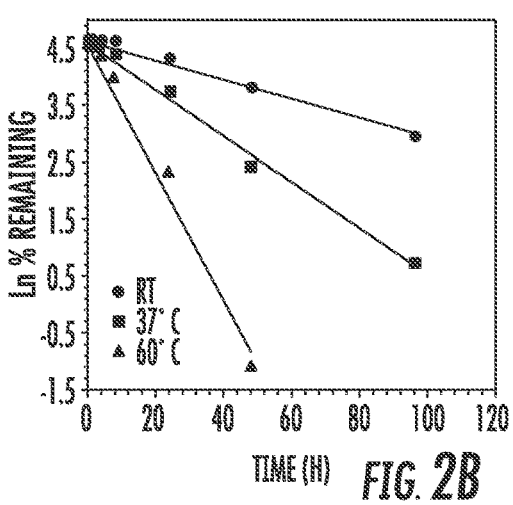
Figure 2C:
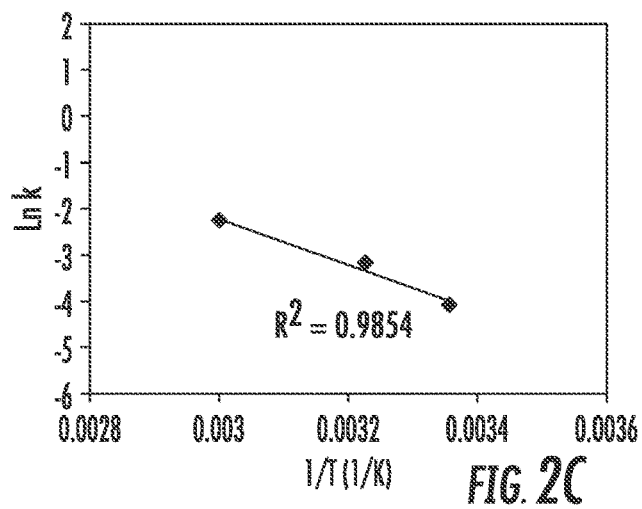

To study the effect of temperature on the chemical stability of Gem-DHA, the Gem-DHA formulation in crimp-sealed vials under nitrogen was stored in room temperature, 37° C., or 60° C., protected from light. Sampling and analyses were carried out at pre-determined time points as described above. The effect of temperature on the chemical stability of Gem-DHA is shown in FIG. 2B. The first order degradation reaction equation was used to calculate the values of the reaction rate (k) at different temperatures (Table 2). An Arrhenius plot was constructed by plotting the ln k values vs. 1/T to calculate the activation energy ($E_a$, in kcal/mol). The activation energy of the chemical reaction was calculated to be 12.86 kcal/mol (FIG. 2C).

TABLE 2

First order degradation rate constant of Gem-DHA in an aqueous formulation at room temperature (~22° C.), 37° C., and 60° C.

| Temperature | k (h$^{-1}$) |
|---|---|
| Room temperature | 0.018 ± 0.001 |
| 37° C. | 0.042 ± 0.005 |
| 60° C. | 0.106 ± 0.009 |

Data shown are mean ± standard deviation (n = 3).

Figure 3A:
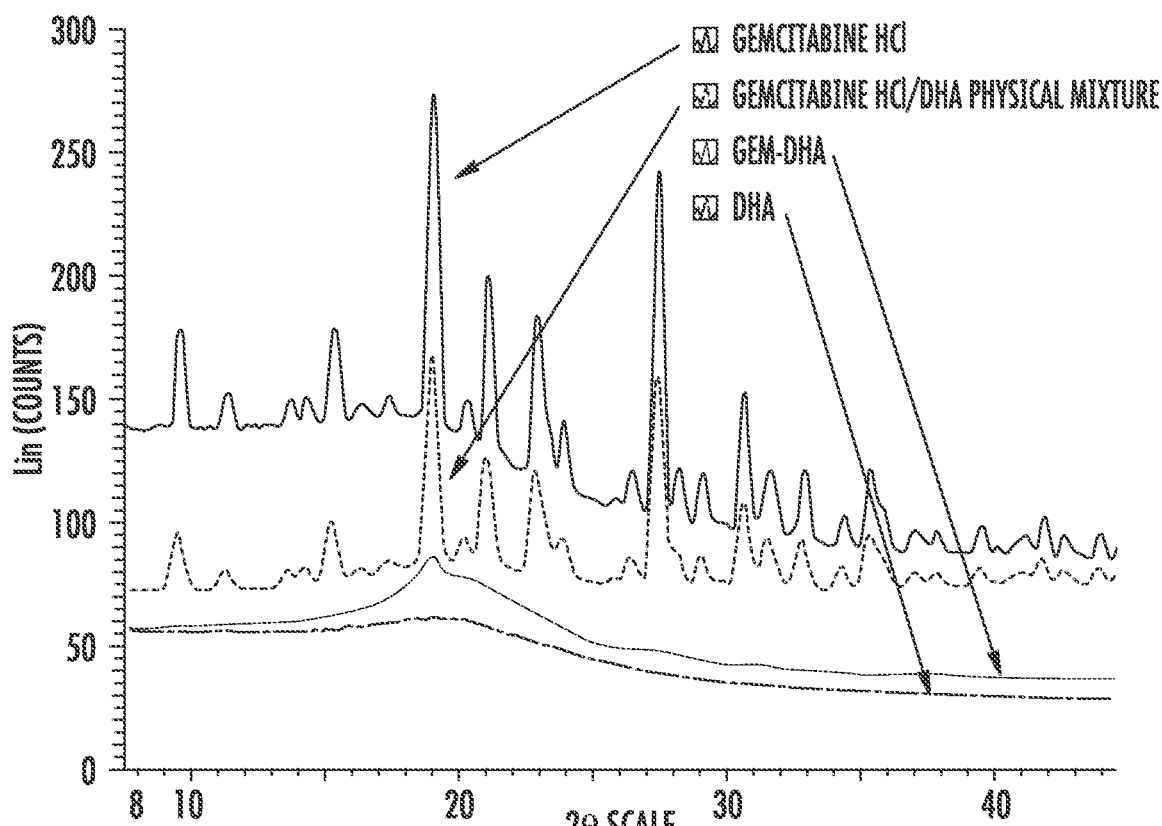
FIG. 3A displays XRD patterns of Gem-DHA, gemcitabine HCl, DHA, and the mixture of gemcitabine HCl and DHA (1:1, m/m).

X-ray diffraction (XRD) analyses of Gem-DHA, gemcitabine HCl, DHA, and the physical mixture of gemcitabine HCl and DHA (1:1, m/m) was carried out using a Rigaku Spider single crystal X-ray diffractometer (Rigaku, Tokyo, Japan). The X-ray diffraction patterns showed that the major crystallinity peaks related to gemcitabine HCl at the 2Θ values of 9.5, 15.4, 19.0, 21.0, 23.0, 27.5, 30.5, and 35.5 were retained in the physical mixture of gemcitabine HCl and DHA, but disappeared in Gem-DHA (FIG. 3A).

Figure 3C:
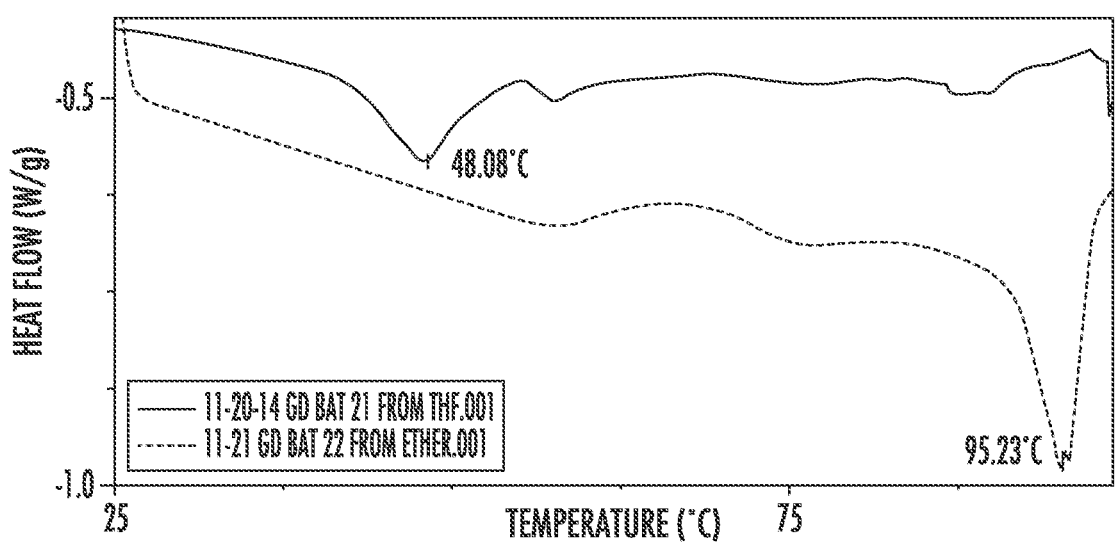
FIG. 3C displays DSC analyses of Gem-DHA precipitated from THF solution (solid line) or ether (dashed line).
Figure 3B:
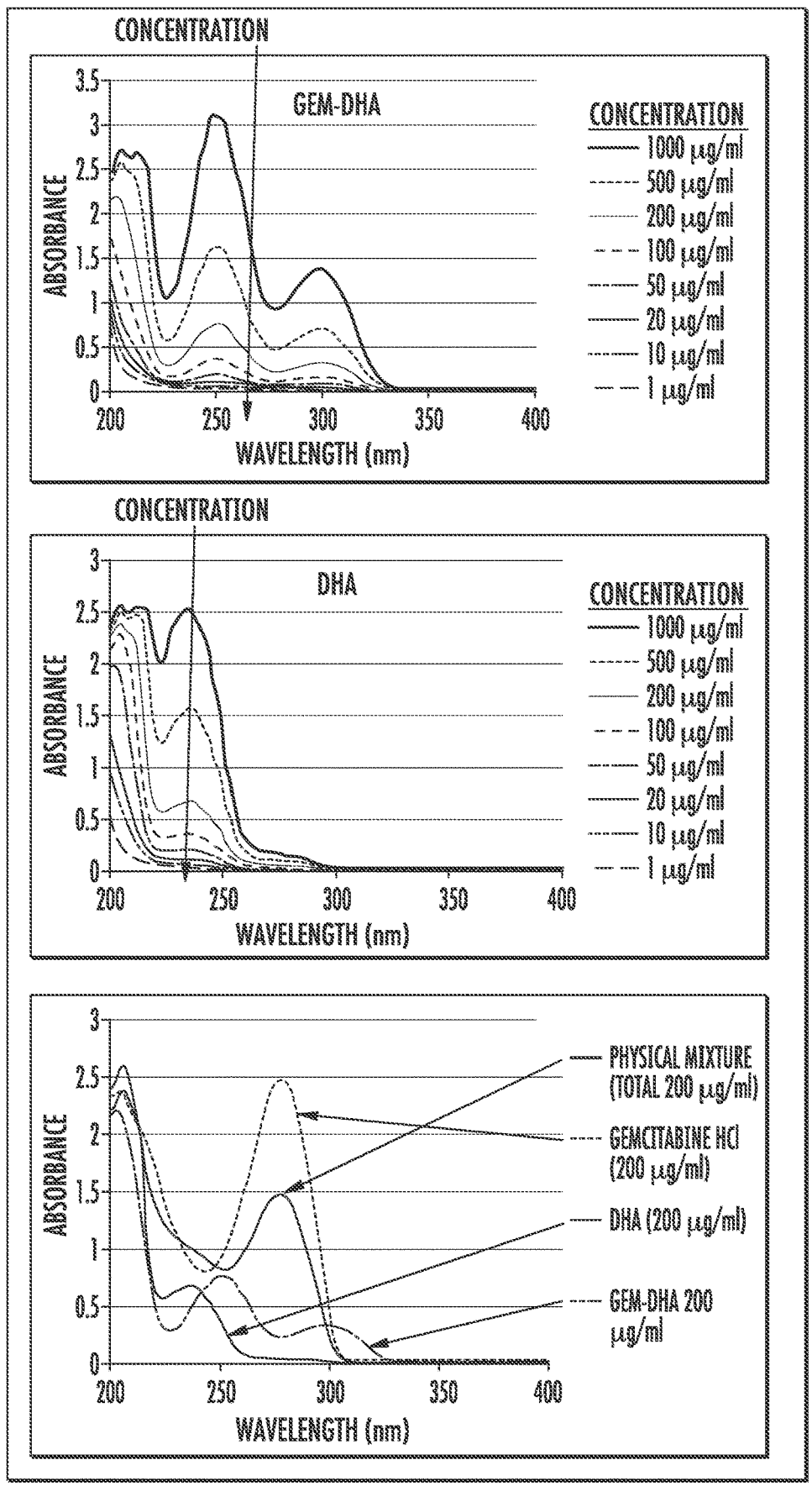
FIG. 3B displays UV/Vis spectra of Gem-DHA and DHA at various concentrations, and a comparison of the UV/Vis spectra of Gem-DHA, gemcitabine HCl, DHA, and the mixture of gemcitabine HCl and DHA.

The UV-Vis absorbance of Gem-DHA, DHA, gemcitabine HCl, and the physical mixture of gemcitabine HCl and DHA, all dissolved in methanol, were evaluated using a BioTek Synery HT Multi-Mode Microplate Reader (Winooski, VT) using the scanning mode. The UV/Vis scanning revealed that the maximum absorption peak ($\lambda_{max}$) of Gem-DHA in methanol was 248 nm, and a secondary absorption peak at 300 nm (FIG. 3B). The $\lambda_{max}$ values of gemcitabine HCl and DHA were 276 nm and 234 nm, respectively (FIG. 3B).

Modulated differential scanning calorimetry (DSC) was used to evaluate the thermal properties of Gem-DHA. Samples (3-5 mg) were placed in sealed pans, and the DSC analysis was carried out using DSC Q200 (TA instruments, New Castle, DE) at a ramp rate of 5° C/min under nitrogen flow. The DSC analysis of Gem-DHA showed a melting point of around 48° C. when it was precipitated from THF, and 95.2° C. when precipitated from diethyl ether (FIG. 3C).

Example 2

Synthesis and Characterization of 4-(N)-Arachidonoyl Gemcitabine (4-(N)-ARA-Gem or Gem-ARA)

Figure 4:
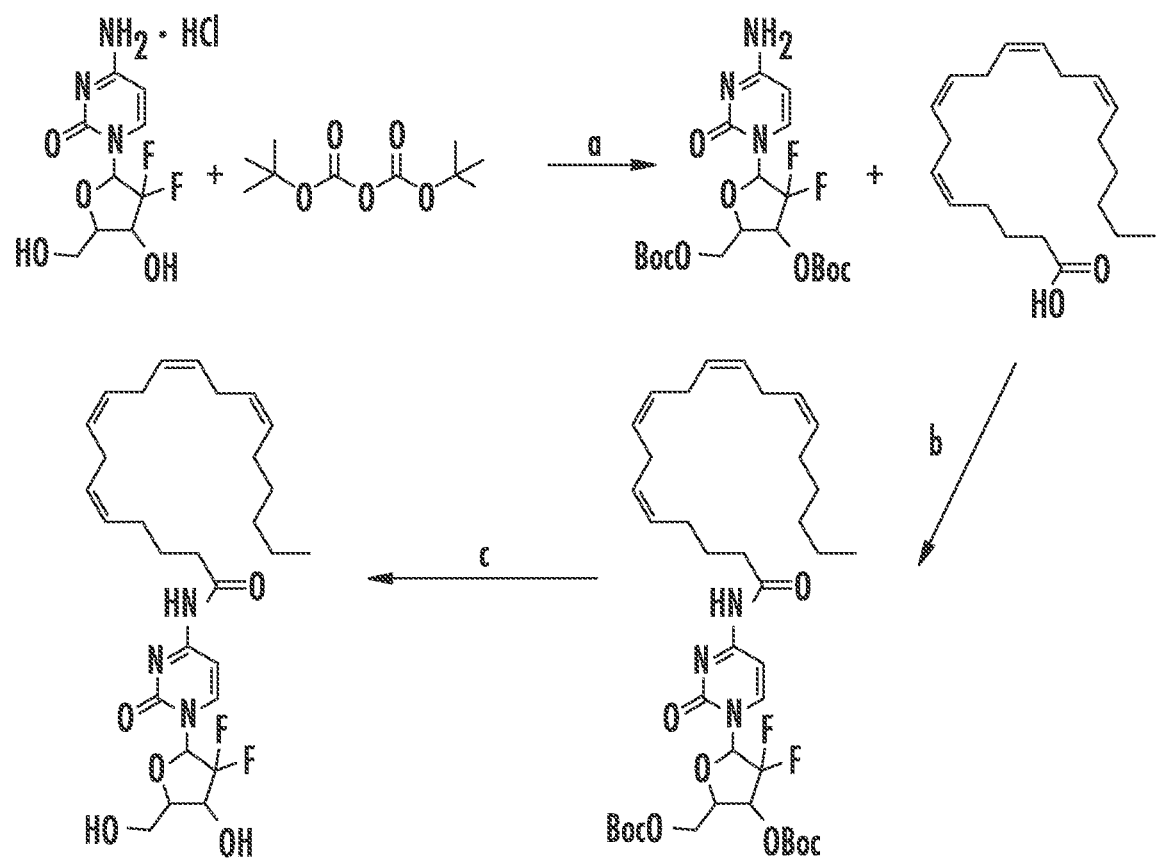
FIG. 4 depicts the synthesis of 4-(N)-ARA-Gem. The reagents and conditions are (a) KOH, 1,4-dioxane, 22° C.; (b) EDCl, HOAt, DCM, room temperature; and (c) TFA, DCM, room temperature.

The 4-(N)-ARA-Gem was synthesized following a protocol similar to the synthesis of 4-(N)-DHA-Gem, except that arachidonic acid (ARA, an omega-6 PUFA), instead of DHA (an omega-3 PUFA), was used to conjugate with 3'-5'-O-bis(tert-butoxycarbonyl) gemcitabine (FIG. 4). $^1$H NMR (300 MHz, THF-d$^4$) δ 10.02 (1H, s, NHCO), 8.15 (1H, d, J=7.2 Hz, 6-CH), 7.36 (1H, d, J=7.2 Hz, 5-CH), 6.25 (1H, t, J=7.4 Hz, 1'-CH), 5.25-5.46 (8H, m, CH), 4.50-4.55 (1H, m, 3'-CH), 3.98-3.70 (3H, m, 4'-CH and 5'-CH$_2$), 2.95-2.78 (6H, m, CH-CH$_2$-CH), 2.45 (2H, t, J=7.7 Hz, CO-CH$_2$), 2.18-2.02 (4H, m, CH-CH$_2$-CH$_2$), 1.42-1.24 (6H, m, CH$_2$-CH$_2$-CH$_2$), 0.89 (3H, t, J=6.3 Hz, terminal CH$_3$). ESI-HRMS [M+Na] +m/z calculated for C$_{29}$H$_{41}$F$_2$N$_3$NaO$_5^+$: 572.2906, found: 572.2912.

Example 3

Figure 5A:
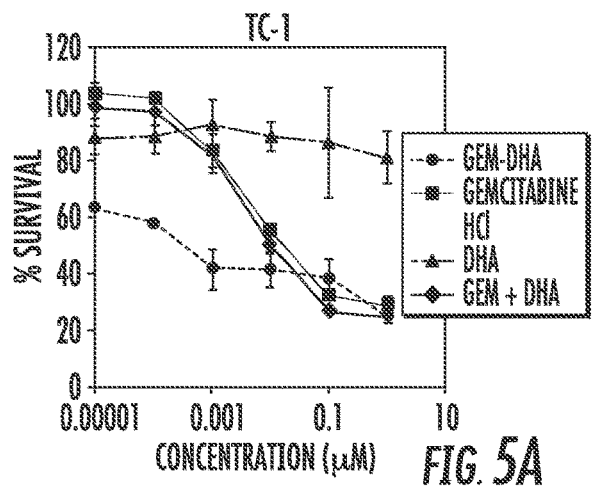
FIG. 5A displays the anti-proliferative activity of Gem-DHA in TC-1 cells determined using an MTT assay.
Figure 5B:
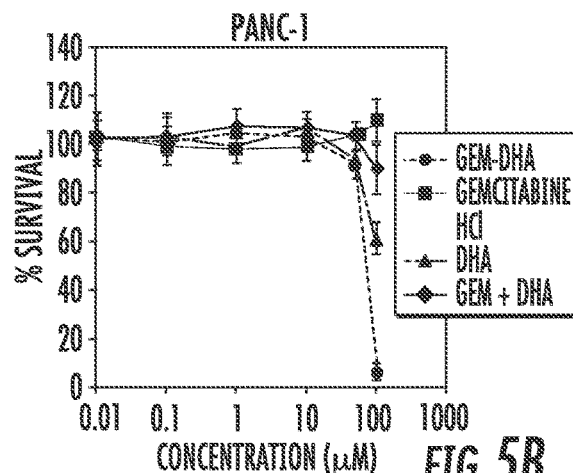
FIG. 5B displays the anti-proliferative activity of Gem-DHA in Panc-1-Luc cells determined using an MTT assay.

Evaluation of the Anti-Proliferative, Cytotoxic, and Apoptotic Activity of Gem-DHA and Gem-ARA Against Tumor Cells in vitro The anti-proliferative activity of Gem-DHA was evaluated in Panc-02, TC-1, Panc-1-Luc, and BxPC-3 cell lines. For Panc-02 and TC-1 cells, cells (1,500/well for Panc-02 and 3,000/well for TC-1) were seeded in 96-well plates and incubated at 37° C. and 5% CO$_2$ overnight. The cells were then treated with various concentrations of Gem-DHA or other compounds for 24 h. For BxPC-3 and Panc-1-Luc cells, 3,000 and 1,000 cells/well were used, respectively, and cells were co-incubated with the Gem-DHA for 72 h. Cell viability was determined using an MTT assay as previously described (Naguib YW et al. *Mol Pharm*. 2014, 11(4), 1239-1249). Gemcitabine HCl was dissolved in cell culture medium, whereas Gem-DHA and DHA were dissolved in dimethylsulfoxide (DMSO). The values of IC$_{50}$ were calculated using GraphPad Prism (GraphPad software, Inc., La Jolla, CA). In both TC-1 mouse lung cancer cells (FIG. 5A) and Panc-1-Luc human pancreatic cells (FIG. 5B), Gem-DHA was more effective than gemcitabine alone or the physical mixture of gemcitabine and DHA (1:1, m/m) in inhibiting tumor cell growth. When evaluated in mouse Panc-02 and human BxPC-3 pancreatic tumor, Gem-DHA again showed a stronger anti-proliferative activity than gemcitabine HCl (Table 3). The IC$_{50}$ value of Gem-DHA was 1.8×10$^5$-fold smaller than that of gemcitabine HCl in Bx-PC3 cells (Table 3).

TABLE 3

IC$_{50}$ values (nM) of Gem-DHA and gemcitabine HCl in BxPc-3 and Panc-02 cells determined using an MTT assay.

| | Gemcitabine HCl | Gem-DHA |
|---|---|---|
| BxPC-3 | 18.5 ± 14.5 | <1.04 × 10$^{-4}$ |
| Panc-02 | 4.0 ± 1.5 | (3.4 ± 3.6) × 10$^{-2}$ |

Figure 6:
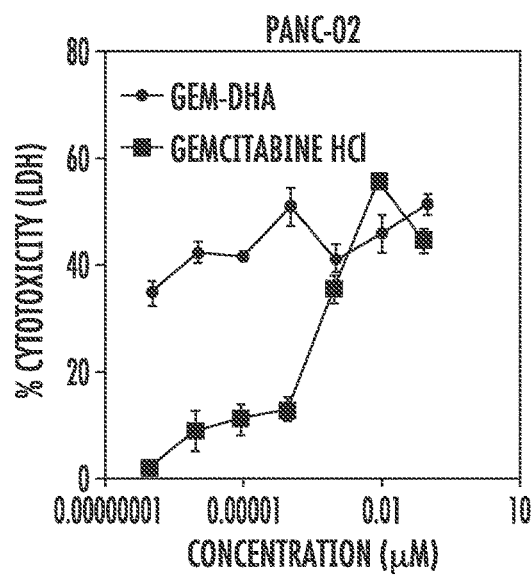
FIG. 6 displays the cytotoxicity of Gem-DHA and gemcitabine HCl in Panc-02 cells determined using an LDH assay.

The cytotoxic activity of Gem-DHA was also evaluated using an LDH assay kit (Takara Clontech). Panc-02 cells were seeded in 96-well plates at 1,500 cells/well and incubated at 37° C. and 5% $CO_2$ for 24 h, followed by treatment with Gem-DHA or gemcitabine HCl as mentioned above for 48 h. LDH activity in the cell culture medium was determined following the manufacturer's instruction. The LDH assay also revealed that Gem-DHA was more cytotoxic than gemcitabine HCl in Panc-02 tumor cells (FIG. 6).

Figure 7:
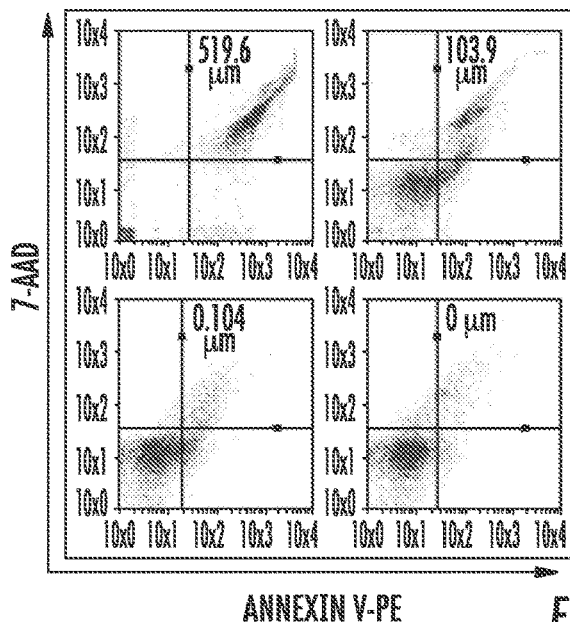
FIG. 7 displays the pro-apoptotic activity of Gem-DHA determined using flow-cytometry after Annexin V staining.

Apoptosis analysis was carried out as previously reported (Zhu S et al. Biomaterials. 2013, 34(9), 2327-2339). Briefly, 100,000 Panc-02 cells were incubated in 24-well plates for 24 h at 37° C. and 5% $CO_2$ and then co-incubated with various concentrations of Gem-DHA for 48 h. The cells were then harvested and stained with 0.1 ml of Guava Nexin reagent (Millipore Corporation, Billerica, Mass.) for 20 min at room temperature, protected from light. The stained cells were analyzed using a Millipore Guava easyCyte 8HT Flow Cytometry System. Control cells were left untreated. Annexin V staining showed that Gem-DHA induced Panc-02 cells to undergo concentration-dependent apoptosis (FIG. 7).

Figure 8:
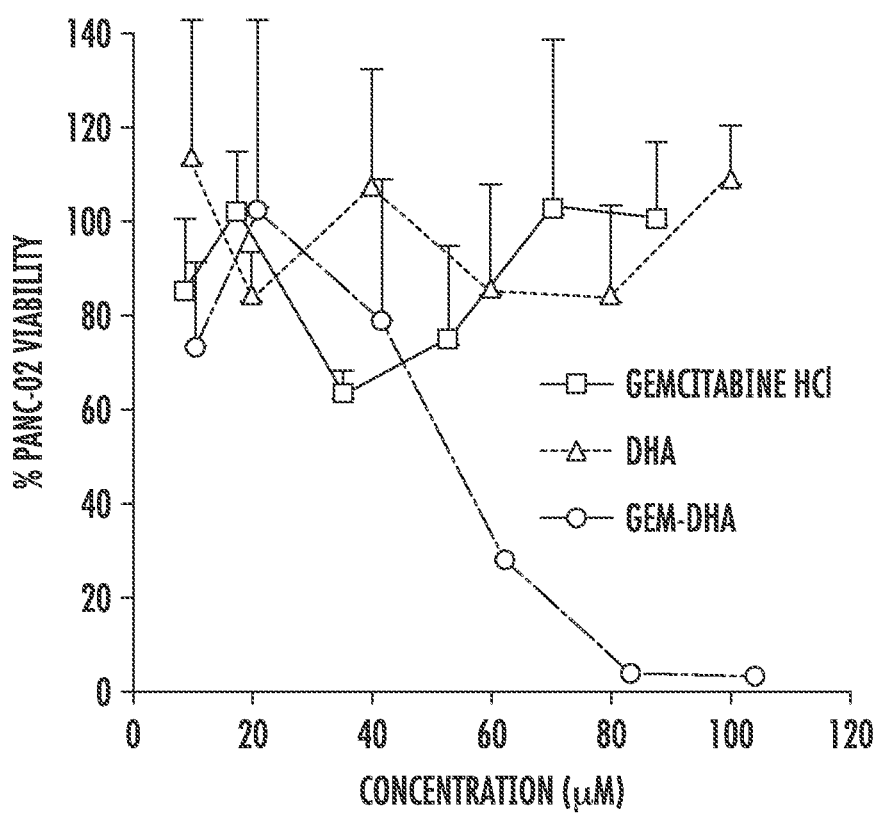
FIG. 8 displays the cytotoxicity of Gem-DHA in Panc-02 tumor cells after 4 h of co-incubation. Cytotoxicity was measured using an MTT assay.

The mechanisms underlying the cytotoxicity of the Gem-DHA may be different from that of gemcitabine. For example, in cell culture studies, Panc-02 cells were seeded into 96-well plates (1,500 cells per well) and incubated at 37° C., 5% $CO_2$ for 24 h. They were then co-incubated with various concentrations of Gem-DHA, gemcitabine HCl alone, or DHA alone for 4 h, and cell viability was determined using an MTT test. As shown in FIG. 8, after only 4 h of co-incubation with Panc-02 tumor cells, Gem-DHA already showed significant cytotoxicity at 60 µM, whereas gemcitabine HCl alone and DHA alone did not show any significant cytotoxicity at concentrations of more than 80 µM.

Figure 9A:
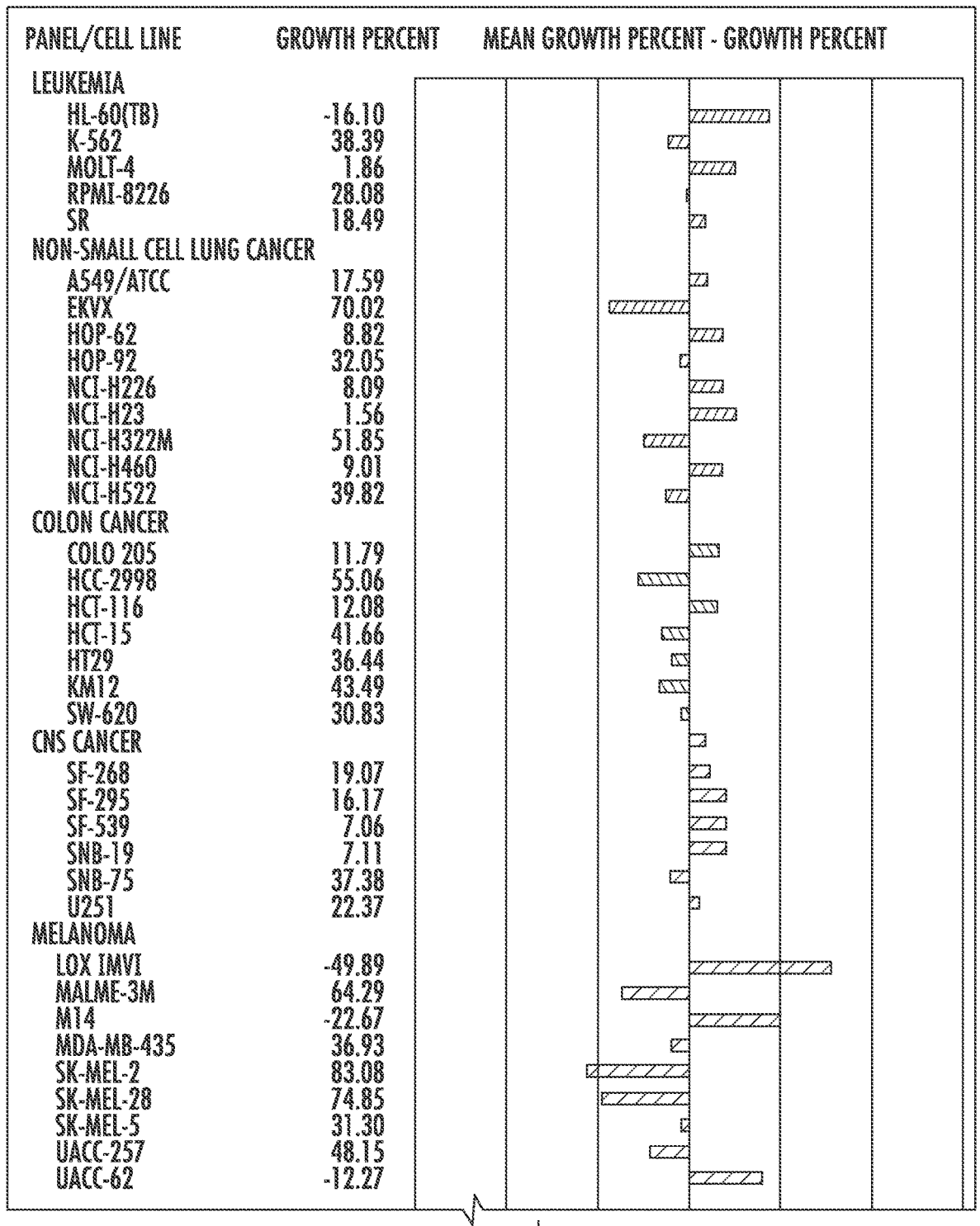
FIG. 9A-FIG. 9B display the results from NCI-60 DTP Human Tumor Cell Line Screen from one dose.
Figure 9B:
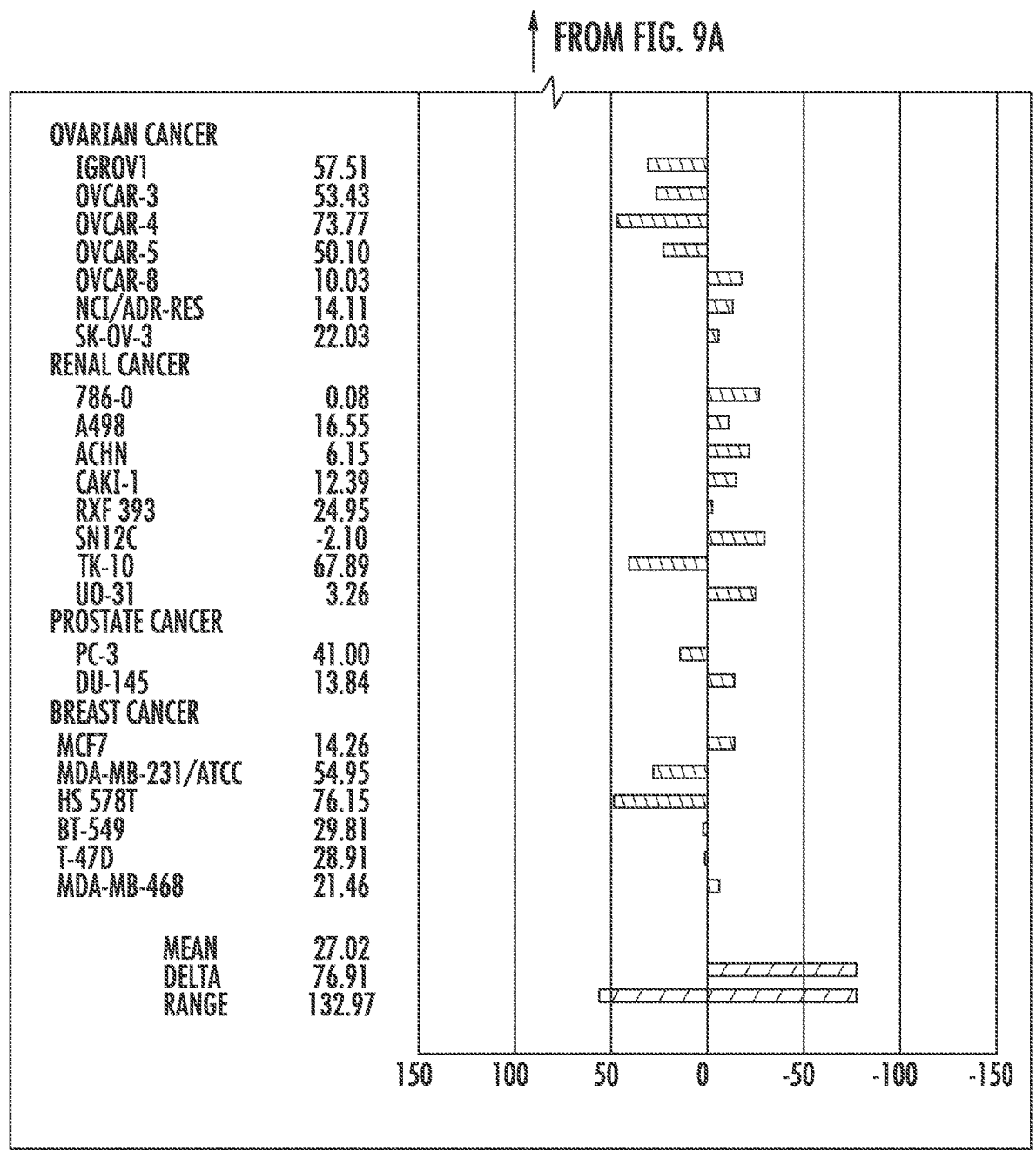

The cytotoxicity of Gem-DHA was also tested using the NCI-60 DTP Human Tumor Cell Line Screen service. The results from the NCI-60 DTP Human Tumor Cell Line Screen at a single dose are shown in FIG. 9A-FIG. 9B.

To understand the effect of the omega-3 polyunsaturated fatty acid nature of the DHA (i.e., the docosahexaedecanoyl group) in the Gem-DHA on its cytotoxicity against tumor cells, gemcitabine was also conjugated to arachidonic acid, an omega-6 polyunsaturated fatty acid, to synthesize 4-(N)-arachidonyl gemcitabine (Gem-ARA) (FIG. 4). Human pancreatic cancer cells (MIA PaCa-2 or BxPC-3) were seeded (3,000/well) in 96-well plates. After overnight incubation, cells were treated with various concentrations of gemcitabine HCl or Gem-ARA at 37° C., 5% CO2 for up to 72 h. Gemcitabine HCl was dissolved in phosphate buffered saline (PBS, pH 7.4, 10 mM), and Gem-ARA was dissolved in DMSO. The maximum amount of DMSO added per well was 0.9 µL, which was found non-toxic. The number of viable cells after the incubation was determined using an MTT assay as described above. The 50% inhibition concentration ($IC_{50}$) values were estimated using GraphPad prism 5 parameters curve fittings. Gem-ARA was not significantly more cytotoxic than gemcitabine HCl when tested in BxPC-3 and MIA PaCa-2 cells (Table 4). Therefore, the conjugation of gemcitabine with a polyunsaturated fatty acid does not necessarily result in a compound with a significantly increased cytotoxicity.

TABLE 4

The $IC_{50}$ values (nM) of Gem-ARA in MIA PaCa-2 and BxPC-3 cells in culture.

| | Gemcitabine HCl | Gem-ARA |
|---|---|---|
| BxPC-3 | 5.52 ± 4.55 | 1.93 ± 3.80 |
| MIA PaCa-2 | 50.2 ± 3.0 | 64.3 ± 42.7 |

Data are mean ± SD (n > 3).

In fact, data from previous studies has also shown that chemically conjugating a saturated fatty acid with gemcitabine does not necessarily result in a compound that is more cytotoxic than gemcitabine. For example, it has been shown that the 4-(N)-stearoyl gemcitabine conjugate (i.e., 4(N) $GemC_{18}$ or $GemC_{18}$) was less cytotoxic than gemcitabine alone in various tumor cell lines in culture (i.e., MIA PaCa-2, Panc-1 cells, CCRF-CEM, B16-F10, and TC-1) (Lansakara-P DSP et al. Int J Pharmaceutics. 2012, 429(1-2), 123-134; Zhu S et al. Bioconj Chem. 2012, 23(5), 966-980). In addition, in mouse models with pre-established tumors, GemC18 (solubilized in a Tween 80 solution) was not more active than gemcitabine alone in inhibiting tumor growth (Brusa P et al. Anticancer Res. 2007, 27(1A), 195-199; Sloat BR et al. Int J Pharmaceutics. 2011, 409(1-2), 278-288; Zhu S et al. Bioconj Chem. 2012, 23(5), 966-980).

DHA has previously been conjugated to paclitaxel, another cancer chemotherapeutical agent, but "the conjugation lowers the cytotoxicity of the paclitaxel" in the NCI-56 human tumor cell lines screen (Bradley E et al. Clin Cancer Res. 2001, 7(10), 3229-3238).

Taken together, Gem-DHA has a broad spectrum, potent antitumor activity. It is not evident that the conjugation of gemcitabine with any fatty acid will lead to a compound that is more cytotoxic than gemcitabine. Similarly, it is not evident that the conjugation of a PUFA such as DHA with any cytotoxic compound will lead to a compound that is more cytotoxic than the parent compound.

Example 4

Evaluation of the Antitumor Activity of Gem-DHA in Animal Models

Nude mice with intrapancreatically injected Panc-1-Luc human pancreatic cancer cells were used as a mouse model of pancreatic cancer. The National Institutes of Health guidelines for animal use and care were followed Animal protocols were approved by the Institutional Animal Care and Use Committee at the University of Texas at Austin. Panc-1-Luc cells (Muniz VP et al. Mol Cancer Res. 2011, 9(7), 867-877) were implanted orthotopically by injecting $1 \times 10^6$ cells into (the tail of) the pancreas.

Panc-1-Luc cell suspension was prepared at a concentration of $2 \times 10^7$ per ml in a 1:1 (v/v) mixture of DMEM and Matrigel. Tumor cells were then injected into the pancreas of male athymic nude mice (6-8 weeks, Charles River Laboratories, Wilmington, Mass.) following a surgical procedure (Raut CP et al. Cancer Biol Ther. 2004, 3(12), 1217-1224; Bruns CJ et al. Neoplasia. 1999, 1(1), 50-62). Briefly, after mice were anesthetized using isoflurane, the skin and peritoneum were cut open about 1 cm in length using sterile surgical scalpels. The pancreas was pulled out, and 50 µL of the cell suspension were injected slowly until a small bleb was formed. After the needle was withdrawn, a small cotton plug was applied for 10 s. The pancreas was returned back, the peritoneum was sutured with Monocryl™ bioresorbable sutures (Ethicon, Somerville, N.J.), and the skin was then closed using surgical clips. Mice were s.c. injected with buprenorphine (0.1 mg/kg) as a pain killer and were left to heal for one week. Tumor progress was monitored using an IVIS™ Spectrum imaging system (Caliper, Hopkinton, MA). For IVIS imaging, each mouse was i.p. injected with a luciferin solution (15 mg/ml) at a dose of 0.15 mg/g body weight in sterile DPBS, anesthetized with isoflurane, and imaged 10 min after luciferin injection. Four weeks after tumor implantation, mice with tumors were randomized into 3 groups (n=5-7) and intraperitoneally injected (i.p) with Gem-DHA (50 mg/kg, ~0.087 mmole/kg), gemcitabine HCl (26.1 mg/kg, ~0.087 mmole/kg), or left untreated. Gem-DHA was in a Tween 80/ethanol/water solution with 5% (w/v) of mannitol, and gemcitabine HCl was in sterile mannitol solution (5%, w/v). Treatments were repeated twice a week for a total 7 doses. Thirty days after the first treatment, mice were sacrificed and tumors were dissected from the pancreas, weighed, and fixed in formalin. The doses were based on the average weight of mice in the same group on the day of injection, and were adjusted only if the weight of an individual mouse was above or below 10% of the average weight.

Figure 10A:
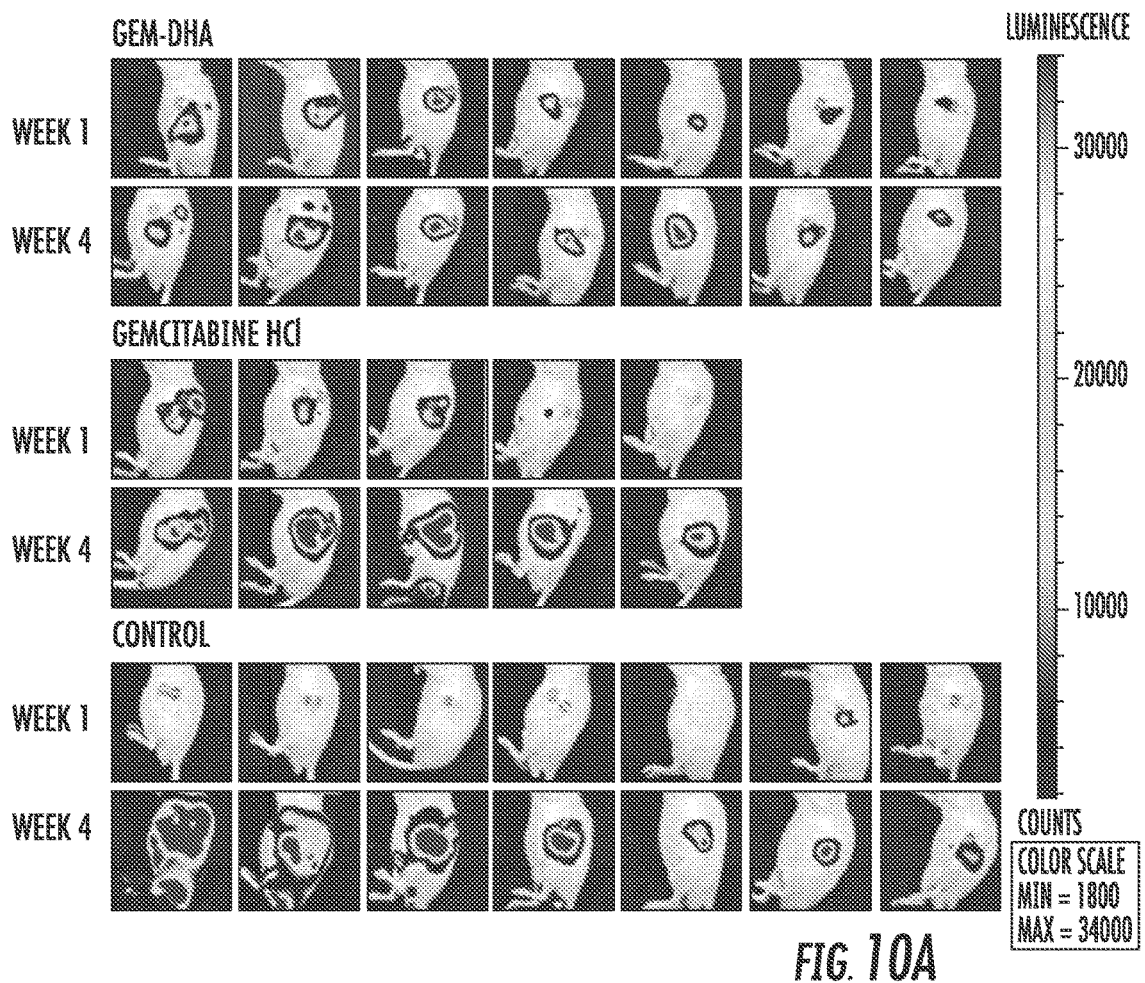
FIG. 10A-FIG. 10D display the antitumor activity of Gem-DHA against Panc-1-Luc tumors in the pancreas of nude mice.
Figure 10B:
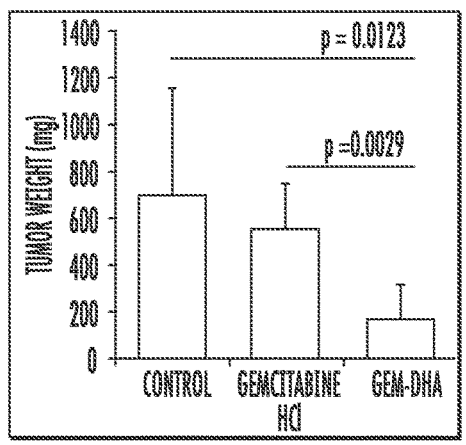
Figure 10C:
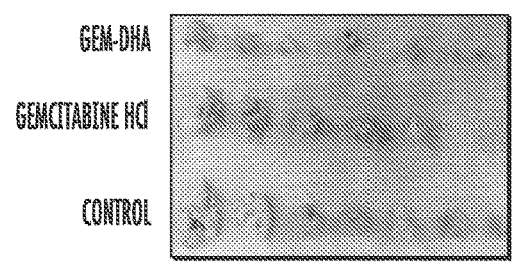
Figure 10D:
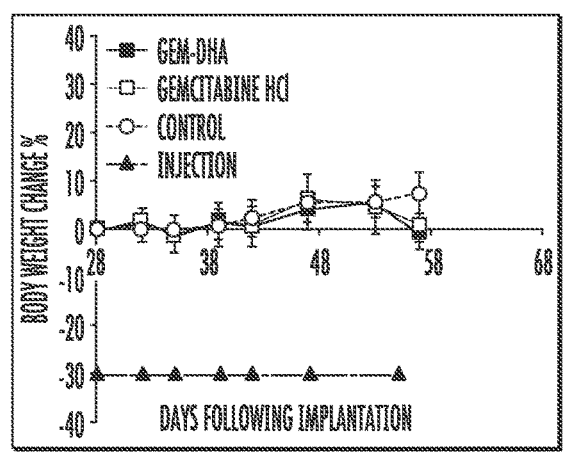

The results showed that Gem-DHA was more effective than the molar equivalent dose of gemcitabine HCl in inhibiting the growth of Panc-1-Luc tumors, but gemcitabine HCl at the dosing regimen used did not significantly inhibit the growth of the Panc-1-Luc tumors (FIG. 10A-FIG. 10C). In fact, by the end of the study, the average weight of tumors in mice that were treated with gemcitabine HCl was not significantly different from that in mice that were left untreated (FIG. 10B).

Figure 11A:
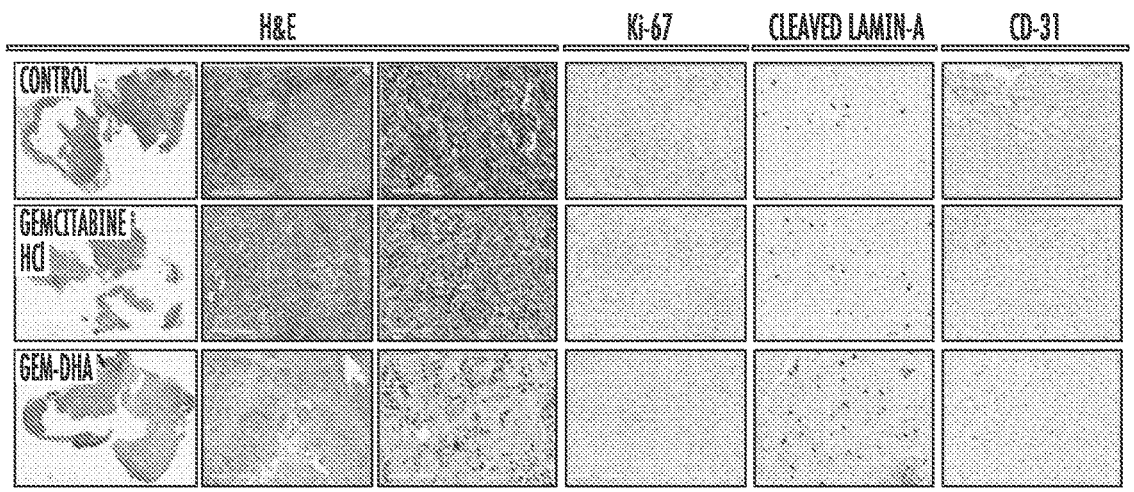
FIG. 11A displays representative histological images of tumors from nude mice that were treated with Gem-DHA or gemcitabine HCl, after the tumor tissues were stained with H&E, anti-Ki-67, anti-cleaved lamin A, or anti-CD31 antibodies.
Figure 11B:
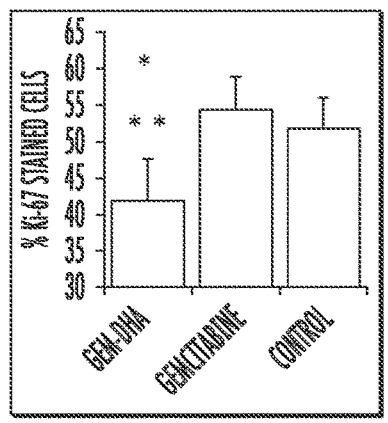
FIG. 11B displays percentage of Ki-67 positively stained cells. (*p<0.05 against control, **p<0.05 against gemcitabine).
Figure 11C:
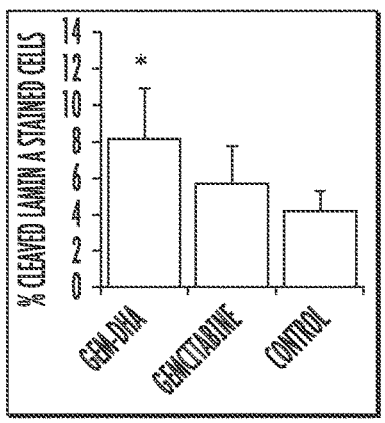
FIG. 11C displays percent of cleaved lamin A positively stained cells (*p<0.05 against control, **p<0.05 against gemcitabine).
Figure 11D:
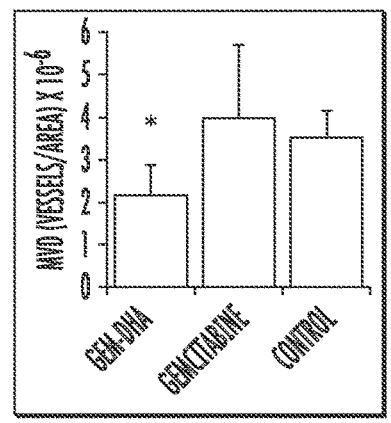
FIG. 11D displays the micro-vessel density (MVD) values in tumors determined after anti-CD-31 staining (*p<0.05 against control, **p<0.05 against gemcitabine).

Tumor tissues were sectioned and stained in the Histology and Tissue Analysis Core at Dell Pediatric Research Institute at the University of Texas at Austin or in the Department of Molecular Carcinogenesis at the University of Texas M.D. Anderson Cancer Center at Science Park (Smithville, Texas) with hematoxylin & eosin (H&E), antibodies against cleaved lamin-A (apoptosis marker), CD-31 (angiogenesis marker), or Ki-67 (proliferation marker). Slides were then scanned, and images were taken using the ScanScope XT (Aperio Technologies, Vista, CA). H&E staining of the tumor tissues revealed that tumors in mice that were left untreated have dense cellular matrix with tightly-packed tumor cells and small intracellular spaces (FIG. 11A). In addition, several areas of necrosis can also be seen in the centers of the tumors. A similar pattern was observed in tumors in mice that were treated with gemcitabine HCl, but with less necrosis. On the contrary, tumors in mice that were treated with Gem-DHA showed less densely packed cancer cells, with a much larger cytoplasm to nucleus ratio and intracellular spaces. Several pyknotic cells with condensed chromatin can also be seen in tumors in mice that were treated with Gem-DHA. Ki-67 staining showed that there is a significantly lower percent of Ki-67 positive cells in tumors in mice that were treated with Gem-DHA than in mice that were treated with gemcitabine HCl (FIG. 11B). Anti-cleaved lamin-A staining showed a significantly higher percent of positive staining in tumors in mice that were treated with Gem-DHA than in mice that were untreated (FIG. 11C), whereas the extent of cleaved lamin-A positive staining in tumors in mice that were treated with gemcitabine HCl was not different from that in mice that were not treated (FIG. 11C). Anti-CD-31 staining showed the microvessel density (MVD) in tumors in mice that were treated with Gem-DHA was significantly lower than in mice that were not treated, but the MVD value in tumors in mice that were treated with gemcitabine HCl was not different from that in mice that were not treated (FIG. 11D).

Figure 12:
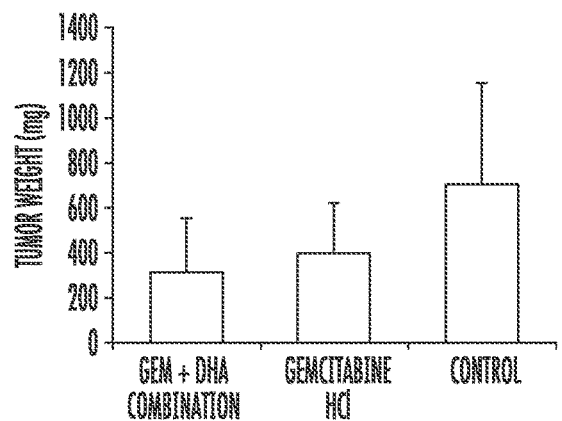
FIG. 12 displays a comparison of the antitumor activities of gemcitabine HCl and the mixture of gemcitabine HCl and DHA against orthotopic Panc-1-Luc tumors in nude mice. Treatments were started two weeks after tumor cell injection and repeated twice a week for a total of 10 times. ANOVA test did not reveal any significant difference among those three groups.

In another experiment, male nude mice with orthotopic Panc-1-Luc tumors were treated 2 weeks after tumor implantation with gemcitabine HCl or a mixture of gemcitabine HCl and DHA, twice a week for a total of 10 times. The doses of both gemcitabine HCl (~33.7 mg/kg) and DHA (~35.3 mg/kg) were about 0.11 mmole/kg. Mice were sacrificed in the $8^{th}$ week after tumor implantation, and the tumors were excised and weighed. The doses were based on the average weight of mice in the same group on the day of injection, and were adjusted only if the weight of an individual mouse was above or below 10% of the average weight. The results showed that treatment of mice with orthotopic Panc-1-Luc tumors with the mixture of gemcitabine HCl and DHA was not significantly more effective than with gemcitabine HCl alone in controlling the tumor growth (FIG. 12), indicating that the simple physical mixture of gemcitabine HCl and DHA, or combination therapy with gemcitabine HCl and DHA, is not as effective as the Gem-DHA chemical conjugate.

There were previous reports that suggested DHA alone has an antitumor activity (Kato T et al. *Nutr Cancer* 2007, 58(2), 178-187; Merendino N et al. *Biomed Res Int*. 2013, 2013, 310186; Rahman MM et al. *Breast Cancer Res Treat*. 2013, 141(3), 341-352; Spencer L et al. *Eur J Cancer* 2009, 45(12), 2077-2086; Strouch MJ et al. *J Surg Res*. 2011, 165(1), 75-81). Therefore, the in vivo anti-tumor activity of Gem-DHA was also evaluated and compared to that of DHA alone in male C57BL/6 mice (6-8 weeks, Charles River) with subcutaneously (s.c.) implanted Panc-02 tumors. Briefly, $1 \times 10^6$ cells were s.c. injected in the right flank of mice. Sixteen days later, mice were randomized into groups (n=12) and i.p. injected with Gem-DHA (~55 mg/kg, -0.1 mmole/kg) or DHA (~33 mg/kg, ~0.1 mmole/kg). Mice in the control group were i.p. injected with sterile 5% mannitol (w/v). Gem-DHA and DHA was dissolved in a Tween 80/ethanol/water solution with 5% (w/v) of mannitol. The doses were based on the average weight of mice in the same group on the first day of injection. The treatment was repeated twice a week for up to 6 doses. Tumor growth was monitored using a digital caliper, and tumor volume was calculated based on the longest diameter ($L_1$) and the shortest diameter ($L_2$) of each tumor using the equation of $V = \frac{1}{2} \times (L_1 \times L_2 \times L_2)$.

Figure 13A:
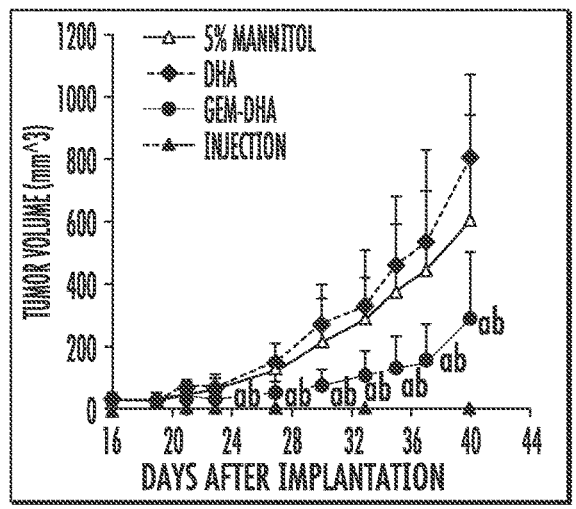
FIG. 13A displays the antitumor activity of Gem-DHA against Panc-02 tumors pre-established in C57BL/6 mice. Data shown are mean±standard derivation (n=12) (p<0.001 vs. DHA).
Figure 13B:
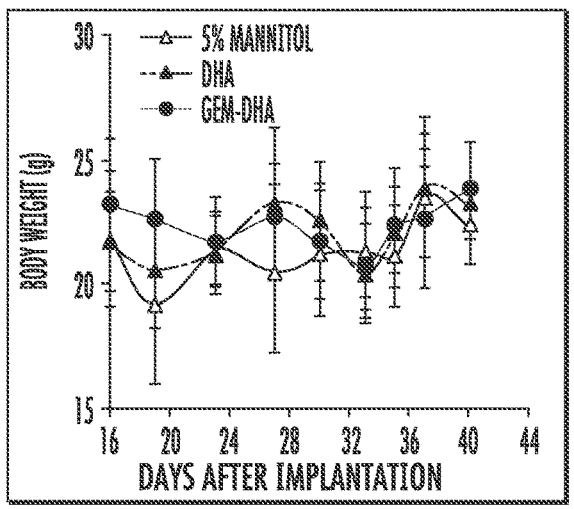
FIG. 13B displays the body weights of Panc-02 tumor-bearing mice. Data shown are mean±standard derivation (n=12) (p<0.01, Gem-DHA vs. 5% mannitol).

As shown in FIG. 13A, treatment of mice with pre-established Panc-02 tumors with Gem-DHA significantly inhibited the tumor growth, but treatment with the molar equivalent dose of DHA alone did not significantly inhibit the tumor growth, demonstrating that the strong antitumor activity of Gem-DHA was not simply due to the docosahexaedecanoyl group in the Gem-DHA. Shown in FIG. 13B are body weights of mice that were treated with Gem-DHA or DHA. It appeared that Gem-DHA at the dosing regimen tested was well tolerated by mice.

Figure 14A:
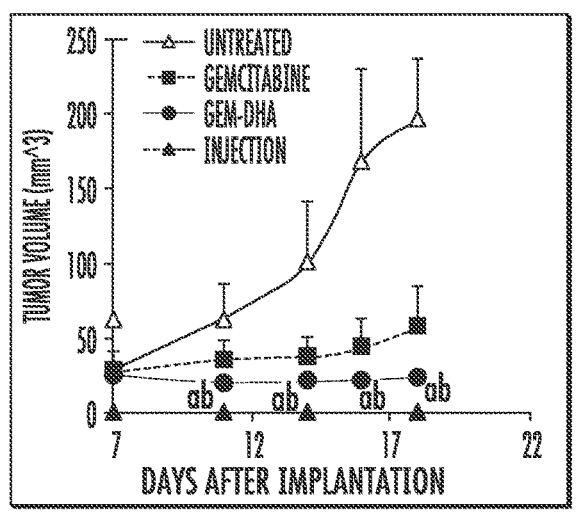
FIG. 14A displays the antitumor activity of Gem-DHA against TC-1 tumors pre-established in C57BL/6 mice. Data shown are mean±standard derivation (n=5-6) (p<0.001 vs. untreated).
Figure 14B:
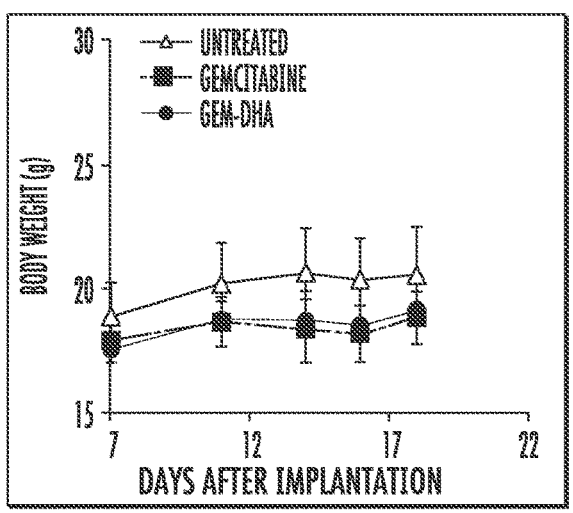
FIG. 14B displays the body weights of TC-1 tumor-bearing mice during the treatments. Data shown are mean±standard derivation (n=5-6) (p<0.05, Gem-DHA vs. gemcitabine HCl).

The NCI-60 DTP Human Tumor Cell Line Screen results showed that Gem-DHA inhibited the growth of various types of human tumor cells (FIG. 9A-FIG. 9B). In addition, the data in FIG. 5A also showed that Gem-DHA was more effective than gemcitabine HCl alone or the mixture of gemcitabine HCl and DHA in inhibiting the growth of the TC-1 mouse lung cancer cells. Therefore, the in vivo antitumor activity of Gem-DHA against TC-1 tumor cells was also evaluated. In the mouse model with TC-1 tumors, $5 \times 10^5$ cells were s.c. injected in the right flank of female C57BL/6 mice (Charles River, 6-8 weeks). Eight days later, mice were randomized into 3 groups (n=5-6) and i.p. injected with Gem-DHA (50 mg/kg, ~0.087 mmole/kg), gemcitabine HCl (26.1 mg/kg, ~0.087 mmole/kg), or left untreated as a control. Treatments were repeated every 3-4 days for a total of 4 times. Tumor growth was monitored and tumor volume was calculated as mentioned above. As shown in FIG. 14A, Gem-DHA was also more effective than a molar equivalent dose of gemcitabine HCl in controlling the growth of s.c. implanted TC-1 tumors, indicating that the antitumor activity of Gem-DHA is not limited to pancreatic tumors. Shown in FIG. 14B are the body weights of TC-1 tumor-bearing mice after they were treated with multiple doses of Gem-DHA.

Figure 15:
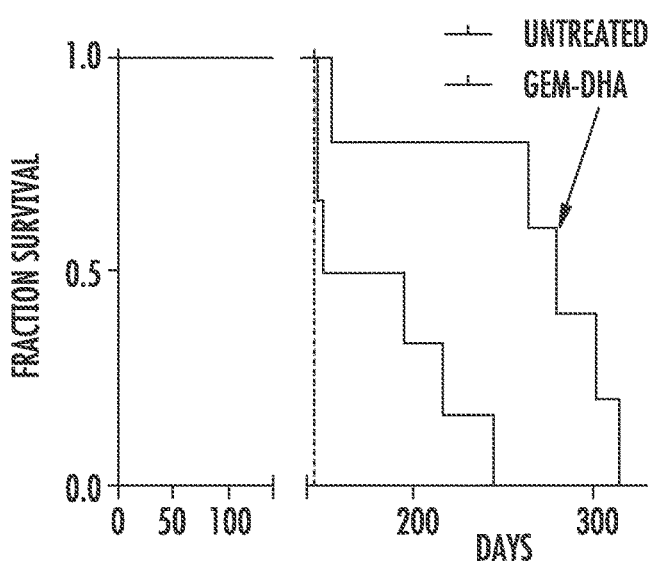
FIG. 15 displays the survival curves of Kras-ink4a transgenic mice that were treated (i.p.) with Gem-DHA or left untreated (p=0.01, Log-rank test).

Finally, the antitumor activity of Gem-DHA was also evaluated in a genetically modified mouse model of pancreatic cancer. Female Kras-Ink4a mice that spontaneously develop pancreatic tumors were obtained from Dr. Stephen Hursting's lab at the University of Texas at Austin (Lashinger L et al. *Cancer Prevention Research*. 2013, 6(10), 1046-1055). Mice were transferred to DIO (diet-induced obesity) diet (D12492 from Research Diets, Inc, New Brunswick, NJ, with 60% kcal fat) on the 15-17$^{th}$ weeks of age, because data from Lashinger et al. showed that DIO diet accelerates the development pancreatic tumors in those mice (Lashinger L et al. *Cancer Prevention Research*. 2013, 6(10), 1046-1055). On the 20th week, one group of mice (n=5) started to receive Gem-DHA (50 mg/kg, in Tween 80/ethanol/water solution with 5% (w/v) of mannitol) by i.p. injection. The injection was repeated twice a week, once a week for the last 5 doses, for a total of 29 times. As a control, another group of mice (n=6) were left untreated. Mouse health was monitored, and any mouse that became moribund or showed a body weight loss of >20% was euthanized. Shown in FIG. 15 are the survival curves of mice treated with Gem-DHA or left untreated. Treatment with Gem-DHA significantly prolonged the survival of the mice. The median survival time of mice that were treated with Gem-DHA was 280 days, in comparison to 172 days for mice that were left untreated (p=0.01, Log-rank (Mantel-Cox) test).

Example 5

Pharmacokinetics and Biodistribution of Gem-DHA

Healthy female C57BL/6 mice (6-8 weeks) were injected intravenously (i.v.) with Gem-DHA solution at a dose of 75 mg/kg via the tail vein. At pre-determined time intervals (5, 15, 30, 60, 120, and 180 min), 3 mice were euthanized at each time point to collect plasma samples. Gem-DHA was extracted twice using ethyl acetate and analyzed using HPLC. Data were analyzed using the Pharsight WinNonlin software (Sunnyvale, Calif.). Pharmacokinetic analysis of plasma Gem-DHA levels in mice following i.v. injection revealed that the elimination of Gem-DHA in plasma follows a bi-exponential model (FIG. 16A). Selected pharmacokinetics parameters are shown in FIG. 16B.

A biodistribution study was carried out in TC-1 tumor-bearing C57BL/6 mice. When tumor diameters reached 7-8 mm (i.e., about 4 weeks after tumor cell injection), mice were injected via the tail vein with a Gem-DHA solution (75 mg/kg). Ninety minutes later, mice were euthanized to collect tumors and major organs (e.g., liver, kidneys, spleen, lung, heart, and pancreas). Tissues were homogenized, and Gem-DHA was extracted using ethyl acetate as mentioned above and analyzed using HPLC. An analysis of the concentrations of Gem-DHA in various organs in TC-1 tumor-bearing mice, 90 min after i.v. injection, showed that a high percent of the injected Gem-DHA was in mouse pancreas, relative to other organs (FIG. 16C).

The biodistribution of Gem-DHA was further evaluated in healthy BALB/c mice. Briefly, female BALB/c mice (Charles River, 14-16 weeks, n=3) were injected via the tail vein with Gem-DHA in a Tween 80/ethanol/water solution containing 5% (w/v) mannitol at a dose of 75 mg/kg. After 1 h, mice were euthanized to collect pancreas, lung, spleen, liver, heart, and kidneys. Gem-DHA was extracted from the samples and analyzed using HPLC. As a control, mice (n=3) were also injected with gemcitabine HCl (75 mg/kg) in 5% (w/v) mannitol solution and euthanized 1 h later to collect their pancreas. Gemcitabine was extracted using the following method. Briefly, once the pancreas was collected, it was weighed, placed into 0.25 ml of PBS containing 40 μg of tetrahydrouridine (a deoxycytidine deaminase inhibitor) and homogenized using a bead beater. Deoxyuridine (dU, 20 μl of 20 μg/ml) was then added into the homogenate as an internal standard. Acetonitrile was used to precipitate the proteins twice, and gemcitabine content in the supernatant was analyzed using HPLC. Similar to what was observed in tumor-bearing C57BL/6 mice (FIG. 16C), in healthy BALB/c mice, the highest percent of the injected Gem-DHA was detected in mouse pancreas (among the organs tested, FIG. 16D). Therefore, it appeared that Gem-DHA preferred to distribute in pancreatic tissues. Finally, a comparison of the content of Gem-DHA or gemcitabine in the pancreas of healthy BALB/c mice that were i.v. injected with Gem-DHA or gemcitabine HCl, respectively, showed that 1 h after injection, 0.37±0.18% of the Gem-DHA was recovered in each gram of pancreas, whereas only 0.07±0.03% of the injected gemcitabine HCl was recovered in each gram of pancreas (FIG. 16E), further indicating that Gem-DHA has an increased accumulation in mouse pancreas, as compared to gemcitabine HCl.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

What is claimed is:

1. A composition comprising a mixture of compounds having Formula II:

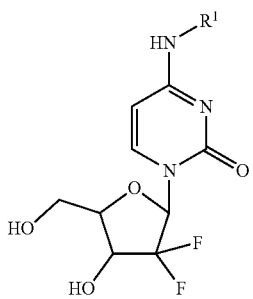

wherein
R¹ comprises an omega-3 polyunsaturated fatty acid having a formula of $CH_3-CH_2-CH=CH-Z-C(O)-$; and
Z is a $C_3$-$C_{40}$ alkenyl group comprising at least one double bond;
or a pharmaceutically acceptable salt thereof.

2. The composition of claim 1, wherein Z is a $C_{20}$-$C_{24}$ alkenyl group comprising at least one double bond.

3. The composition of claim 1, wherein the omega-3 polyunsaturated fatty acid is chosen from docosahexaenoic acid, docosapentaenoic acid, eicosapentaenoic acid, alpha-linolenic acid, or any combination thereof.

4. The composition of claim 1, wherein the omega-3 polyunsaturated fatty acid is chosen from hexadecatrienoic acid, stearidonic acid, eicosatrienoic acid, eicosatetraenoic acid, heneicosapentaenoic acid, tetracosapentaenoic acid, or tetracosahexaenoic acid.

5. The composition of claim 1, wherein the composition comprises a compound having Formula III:

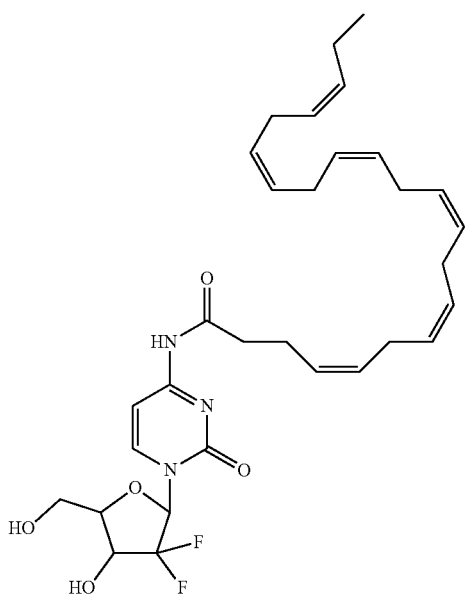

or a pharmaceutically acceptable salt thereof.

6. The composition of claim 1, wherein the composition comprises a compound having Formula IV:

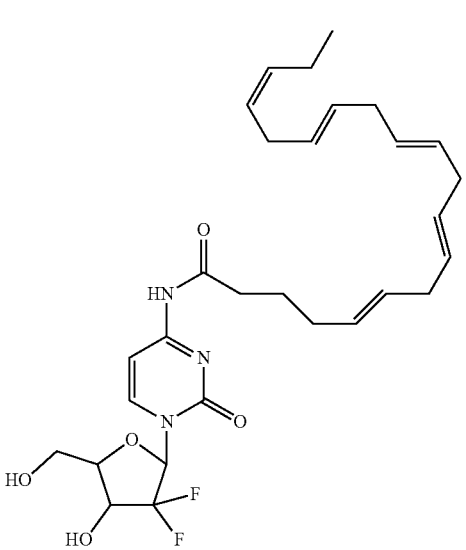

or a pharmaceutically acceptable salt thereof.

7. A pharmaceutical composition comprising the composition of claim 1 and a pharmaceutically acceptable carrier, an excipient, or a combination thereof.

8. The pharmaceutical composition of claim 7, wherein the pharmaceutical composition is a liquid mixture.

9. The composition of claim 1, wherein the composition includes a mixture of two or more compounds of Formula II having different R¹ groups.

10. The composition of claim 1, wherein the composition comprises a mixture of three or more compounds of Formula II having different R¹ groups.

11. The composition of claim 1, wherein the composition comprises a first compound wherein the omega-3 polyunsaturated fatty acid is docosahexaenoic acid and a second compound wherein the omega-3 polyunsaturated fatty acid is eicosapentaenoic acid.

12. The composition of claim 1, wherein the composition comprises a first compound wherein the omega-3 polyunsaturated fatty acid is docosahexaenoic acid, a second compound wherein the omega-3 polyunsaturated fatty acid is eicosapentaenoic acid, and a third compound wherein the omega-3 polyunsaturated fatty acid is alpha-linolenic acid.

13. The composition of claim 1, wherein the composition comprises a first compound wherein the omega-3 polyunsaturated fatty acid is docosahexaenoic acid and a second compound wherein the omega-3 polyunsaturated fatty acid is heneicosapentaenoic acid.

14. The composition of claim 1, wherein the composition comprises a first compound wherein the omega-3 polyunsaturated fatty acid is docosahexaenoic acid and a second compound wherein the omega-3 polyunsaturated fatty acid is tetracosahexaenoic acid.

15. The composition of claim 1, wherein the composition comprises a first compound wherein the omega-3 polyunsaturated fatty acid is docosahexaenoic acid, a second compound wherein the omega-3 polyunsaturated fatty acid is heneicosapentaenoic acid, and a third compound wherein the omega-3 polyunsaturated fatty acid is tetracosahexaenoic acid.

16. The composition of claim 1, wherein the composition is a liquid mixture.

17. A method for treating a cancer, cachexia, a viral infection, or a combination thereof, the method comprising administering to a subject a therapeutically effective amount of the composition of claim 1.

18. The method of claim 17, wherein the composition is administered orally, intravenously, or a combination thereof.

19. The method of claim 17, wherein the composition is administered utilizing liposome technology.

20. The method of claim 17, wherein the method comprises treating a cancer and the cancer comprises pancreatic, breast, non-small cell lung, or ovarian cancer.

* * * * *